(12) United States Patent
Wimberly

(10) Patent No.: US 8,428,884 B1
(45) Date of Patent: Apr. 23, 2013

(54) PROTEIN SYNTHESIS MODULATORS

(75) Inventor: Brian T. Wimberly, Guilford, CT (US)

(73) Assignee: Rib-X Pharmaceuticals, Inc., New Haven, CT (US)

( * ) Notice: Subject to any disclaimer, the term of this patent is extended or adjusted under 35 U.S.C. 154(b) by 932 days.

(21) Appl. No.: 12/074,200

(22) Filed: Feb. 29, 2008

Related U.S. Application Data

(63) Continuation of application No. 10/889,378, filed on Jul. 12, 2004, now abandoned.

(60) Provisional application No. 60/490,460, filed on Jul. 28, 2003, provisional application No. 60/487,371, filed on Jul. 14, 2003.

(51) Int. Cl.
*G06F 7/00* (2006.01)

(52) U.S. Cl.
USPC .................. 702/19; 702/20; 703/11; 707/700

(58) Field of Classification Search .................. None
See application file for complete search history.

(56) References Cited

U.S. PATENT DOCUMENTS

| | | | |
|---|---|---|---|
| 6,638,908 B1 | 10/2003 | Steitz et al. | |
| 6,925,394 B2 | 8/2005 | Ramakrishnan et al. | |
| 6,939,848 B2 | 9/2005 | Steitz et al. | |
| 6,947,844 B2 * | 9/2005 | Steitz et al. | 702/19 |
| 6,947,845 B2 * | 9/2005 | Steitz et al. | 702/19 |
| 6,952,650 B2 | 10/2005 | Steitz et al. | |
| 6,969,726 B2 | 11/2005 | Lou et al. | |
| 7,079,956 B2 | 7/2006 | Ramakrishnan et al. | |
| 7,133,783 B2 | 11/2006 | Noller et al. | |
| 7,504,486 B2 | 3/2009 | Steitz et al. | |
| 7,666,849 B2 | 2/2010 | Steitz et al. | |
| 2002/0086308 A1 * | 7/2002 | Steitz et al. | 435/6 |
| 2003/0232779 A1 | 12/2003 | Steitz et al. | |
| 2005/0153971 A1 | 7/2005 | Chen et al. | |
| 2005/0203147 A1 | 9/2005 | Zhou et al. | |
| 2005/0234227 A1 | 10/2005 | Steitz et al. | |
| 2005/0272681 A1 | 12/2005 | Steitz et al. | |
| 2006/0136146 A1 | 6/2006 | Steitz et al. | |
| 2010/0131258 A1 | 5/2010 | Steitz et al. | |
| 2010/0204253 A1 | 8/2010 | Steitz et al. | |
| 2010/0312525 A1 | 12/2010 | Steitz et al. | |

OTHER PUBLICATIONS

Ban et al., "The Complete Atomic Structure of the Large Ribosomal Subunit at 2.4 Å Resolution" Science, vol. 289, (Aug. 11, 2000) pp. 905-920.
Harms et al., "High Resolution Structure of the Large Ribosomal Subunit from a *Mesophilic eubacterium*" Cell, vol. 107, (Nov. 30, 2001), pp. 679-688.
Nissen et al., "The Structural Basis of Ribosome Activity in Peptide Bond Synthesis" Science, vol. 289, (Aug. 11, 2000), pp. 920-930.
Schuwirth et al., "Structures of the Bacterial Ribosome at 3.5 Å Resolution" Science, vol. 310, (Nov. 4, 2005), pp. 827-834.
Schuwirth et al., "Supporting Online Material for Structures of the Bacterial Ribosome at 3.5 Å Resolution" Science, vol. 310, issue 827, (Nov. 4, 2005),supporting online material for preceding reference, pp. 1-26.
Schluenzen et al., "Structure of Functionally Activated Small Ribosomal Subunit at 3.3 Å Resolution" Cell, vol. 102, (Sep. 1, 2000), pp. 615-623.
Selmer et al, "Structure of the 70S Ribosome Complexed with mRNA and tRNA" Sciencexpress, (Sep. 7, 2006), pp. 1-8 and figures 1-6.
Wimberly et al., "Structure of the 30S Ribosomal Subunit" Nature, vol. 407, (Sep. 21, 2000), pp. 327-339.
Yusupov et al., "Crystal Structure of the Ribosome at 5.5 Å Resolution" Science, vol. 292, (May 4, 2001), pp. 883-896.
Schmeing et al., "Structures of deacylated tRNA mimics bound to the E site of the large ribosomal subunit" RNA, vol. 9, (2003), pp. 1345-1352.

* cited by examiner

*Primary Examiner* — Mary Zeman
(74) *Attorney, Agent, or Firm* — Goodwin Procter LLP

(57) ABSTRACT

The invention provides a high resolution three-dimensional structure of a deacylated transfer RNA protein synthesis modulator in association with a large ribosomal subunit. The protein synthesis modulator binds at least a portion of the E-site of a large ribosomal subunit. The invention provides methods for designing and/or identifying analogs of candidate molecules, for example, analogs or derivatives of the protein synthesis modulator, that bind and/or modulate the protein biosynthetic activity of the ribosome.

15 Claims, 5 Drawing Sheets
(2 of 5 Drawing Sheet(s) Filed in Color)

PROTEIN SYNTHESIS MODULATORS

RELATED APPLICATIONS

This application is a continuation of U.S. patent application Ser. No. 10/889,378, filed Jul. 12, 2004, and claims the benefit of the filing date of U.S. provisional patent application Ser. No. 60/490,460, filed Jul. 28, 2003 and U.S. provisional patent application Ser. No. 60/487,371, filed Jul. 14, 2003, the entire disclosures of each of which are incorporated by reference herein.

FIELD OF THE INVENTION

The present invention relates to the field of ribosome modulators, for example, inhibitors of protein biosynthesis, and to methods of making and using such modulators. More particularly, the invention relates to the three-dimensional structures of deacylated transfer RNA-based protein synthesis modulators, either alone or when associated with a large ribosomal subunit, the modulator's binding site within a large ribosomal subunit, and to methods of making and using protein synthesis modulators that associate with the binding site to modulate ribosome function.

BACKGROUND

The evolution of strains of cells or organisms resistant to currently effective therapeutic agents is an ongoing medical problem. For example, the development of cancerous cells resistant to certain anti-proliferative agents, such as chemotherapeutic drugs, has long been recognized as a problem in the oncology field. Once resistant cells develop, the therapeutic regime must be modified to introduce other, effective anti-proliferative agents. Another example of resistance is the development of strains of microbial, fungal, parasitic and viral pathogens resistant to one or more anti-infective agents. The problem of resistance to anti-infective agents is particularly problematic for antibiotic therapy. Over the past several decades, an increasing number of bacterial strains have developed resistance to one or more antibiotic agents. Accordingly, there is a need for new anti-proliferative and anti-infective agents that are effective against strains of cells or organisms that have developed resistance to currently available agents. One approach to developing improved anti-proliferative and anti-infective agents is to provide modulators (for example, inhibitors) of ribosome function.

Ribosomes are ribonucleoproteins, which are present in both prokaryotes and eukaryotes. Ribosomes are the cellular organelles responsible for protein synthesis. During gene expression, ribosomes translate the genetic information encoded in a messenger RNA into protein (Garrett et al. (2000) "The Ribosome: Structure, Function, Antibiotics and Cellular Interactions," American Society for Microbiology, Washington, D.C.).

Ribosomes comprise two nonequivalent ribonucleoprotein subunits. The larger subunit (also known as the "large ribosomal subunit") is about twice the size of the smaller subunit (also known as the "small ribosomal subunit"). The small ribosomal subunit binds messenger RNA (mRNA) and mediates the interactions between mRNA and transfer RNA (tRNA) anticodons on which the fidelity of translation depends. The large ribosomal subunit catalyzes peptide bond formation—the peptidyl-transferase reaction of protein synthesis—and includes, at least, three different tRNA binding sites known as the aminoacyl, peptidyl, and exit sites. The aminoacyl site or A-site accommodates the incoming aminoacyl-tRNA that is to contribute its amino acid to the growing peptide chain. The peptidyl site or P-site accommodates the peptidyl-tRNA complex, i.e., the tRNA with its amino acid that is part of the growing peptide chain. The exit or E-site accommodates the deacylated tRNA after it has donated its amino acid to the growing polypeptide chain.

The tRNA molecule typically comprises from about 75 to about 90 nucleotides, wherein certain tRNA molecules become charged with or carry a specific amino acid. The tRNA molecule usually is represented by a two dimensional "clover leaf" (see, FIG. 1). The tRNA clover leaf comprises: an aminoacyl acceptor stem which includes a highly conserved 3' terminal adenine nucleotide; a D stem-loop, which is so named because it generally comprises one or more dehydrouridine nucleotides; an anticodon stem-loop, which comprises a variable 3-nucleotide anticodon which base pairs (via hydrogen bonds) to a complementary mRNA codon; and a "T" stem-loop, which is so named because it often contains a ribothymidine. The aminoacyl acceptor stem includes a 3' terminal adenosine, which by convention is designated A76, and which covalently binds to the amino acid it carries via an acyl linkage.

Because the E-site of the large ribosomal subunit plays a key role in protein biosynthesis, the E-site, like the A- and P-sites, provides an important target site for the design of modulators of protein biosynthesis, such as new anti-infective, anti-proliferative, and anti-inflammatory agents.

SUMMARY OF THE INVENTION

The present invention is based, in part, upon the determination of the three-dimensional atomic structure of certain deacylated transfer RNA-based protein synthesis modulators when they are associated with the large subunit of the ribosome. The protein synthesis modulator, also referred to herein as an RNA microhelix or an RNA minihelix is a mimetic of an aminoacyl acceptor stem of a deacylated tRNA molecule, which when bound to the large subunit of the ribosome binds to at least a portion of the E-site of the large ribosomal subunit.

The studies described hereinbelow now define a high resolution structure (i.e., better than 4.0 Å resolution, and more preferably better than 3.5 Å resolution) of at least a portion of the E-site of the large ribosomal subunit. The invention provides a computer system containing data indicative of atomic co-ordinates defining at least a portion of a RNA microhelix binding site of the large ribosomal subunit, either alone or in combination with a RNA microhelix. In addition, the invention provides methods of using the atomic co-ordinates to identify candidate molecules that selectively target and/or bind a ribosome, and preferentially modulate (e.g., inhibit or reduce) the activity of the ribosome in protein biosynthesis (i.e., acts as a selective inhibitor of protein biosynthesis). Each of these aspects and features of the invention are discussed in more detail below.

In one aspect, the invention provides a computer system useful for designing, testing and refining new candidate molecules via rational drug design. The computer system comprises: (a) a memory having stored therein data indicative of atomic co-ordinates defining at least a portion of an RNA microhelix binding site of a large subunit of a ribosome and atomic co-ordinates defining at least a portion of an RNA microhelix molecule in association with the RNA microhelix binding site; and (b) a processor in electrical communication with the memory. The processor comprises a program for generating a three-dimensional model representative of at least a portion of the RNA microhelix binding site and at least a portion of the RNA microhelix molecule. The computer may further comprise a device, for example, a monitor or terminal, for providing a visual representation of the model. The processor optimally further comprises one or more programs to facilitate rational drug design.

The RNA microhelix binding site can comprise at least a portion of an E-site and can be defined by a plurality of residues set forth in Table 1 or Table 2. The atomic co-ordinates can comprise at least a portion of the atomic co-ordinates recorded on Disk No. 1 under file name microhelix.pdb or microhelixa.pdb, or may be produced by molecular modeling, for example, by homology modeling or molecular replacement from such co-ordinates.

In another aspect, the invention provides a computer system comprising: (a) a memory having stored therein data indicative of atomic co-ordinates defining at least a portion of an RNA microhelix binding site of a large subunit of a ribosome and comprising at least one residue selected from the group consisting of Lysine-54, Valine-55, Proline-56, Glycine-57, and Glycine-58 from *Haloarcula marismortui* ribosomal protein L44E or a homolog thereof having at least 55% sequence identity with the *Haloarcula marismortui* ribosomal protein L44E; and (b) a processor in electrical communication with the memory. The foregoing amino acid residues belonging to ribosomal protein L44E undergo conformational change or otherwise more move upon binding of the RNA microhelix.

The processor comprises a program for generating a three-dimensional model representative of the microhelix binding site or a portion thereof and also of the RNA microhelix or a portion thereof in association with the microhelix binding site or a portion thereof. The processor optionally further comprises one or more programs to facilitate rational drug design. The computer system optionally further comprises a device, for example, a computer monitor or terminal, for providing a visual representation of the molecular model.

The atomic co-ordinates of two examples of microhelices in association with the large ribosomal subunit, i.e. two microhelix-ribosome complexes of the present invention, are provided herein. In one instance the atomic co-ordinates defining the three-dimensional structure of the RNA microhelix of Formula I in association with the large ribosomal subunit are recorded on compact disk, Disk No. 1, under file name microhelix.pdb.

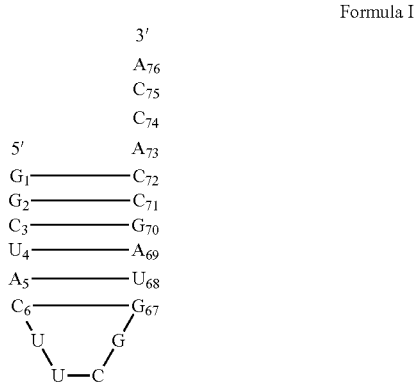

(SEQ ID NO.: 1).

In another instance the atomic co-ordinates defining the three-dimensional structure of the RNA microhelix of Formula II in association with the large ribosomal subunit defining the microhelix site are recorded on compact disk, Disk No. 1, under file name microhelixa.pdb.

Also, a set of atomic co-ordinates defining the three-dimensional structure of the large ribosomal subunit in the absence of a RNA microhelix are recorded on compact disk, Disk No. 1, under file name 1 JJ2.pdb.

The skilled artisan, using the atomic co-ordinates provided herein, can generate models of a ribosomal subunit of interest using conventional molecular modeling techniques including, for example, homology modeling and/or molecular replacement techniques. The models can then be used for the rational design of candidate molecules that are protein synthesis modulators.

The RNA microhelix binding site is defined by a plurality of residues set forth in Table 1 or Table 2. A plurality of residues shall be considered to include at least 3 residues, preferably at least 5 residues, and more preferably at least 10 residues. The binding site can be defined by atoms of ribosomal RNA, one or more ribosomal proteins, or a combination of ribosomal RNA and one or more ribosomal proteins.

The RNA microhelix can be used as a structural probe for identifying at least a portion of the E-site and/or identifying a subset of the large ribosomal subunit residues that together define a portion of the E-site. The RNA microhelix can comprise, for example, one, two three, or four ribonucleotides independently selected from the group consisting of $A_{76}$, $C_{75}$, $C_{74}$, and $N_{73}$, wherein N is a ribonucleotide selected from the group consisting of adenosine, guanosine, cytidine, and uridine. Alternatively, the RNA microhelix can comprise ribonucleotides $A_{76}$ and $C_{75}$, optionally having the structure

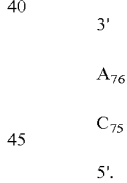

In the forgoing structure and further structures herein the 3' and 5' designations are used in their conventional sense to depict the directionality of nucleotides in the polynucleotide. See, Biochemistry, 2" Edition, Geoffrey Zubay (coordinating author), Chapter 7 *Nucleotides and Nucleic Acids* (MacMillan Publishing Co., New York, N.Y. 1988).

Alternatively, the RNA microhelix can comprise ribonucleotides $A_{76}$, $C_{75}$, and $C_{74}$, and optionally having the structure

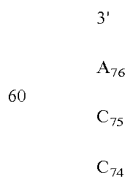

Alternatively, the RNA microhelix can comprise ribonucleotides $A_{76}$, $C_{75}$, $C_{74}$, and $N_{73}$, wherein N is a ribonucleotide selected from the group consisting of adenosine, guanosine, cytidine, and uridine, and optionally having the structure

Alternatively, the RNA microhelix can comprise the structure

wherein n=0 or 1 and p=0 or 1, and N is a ribonucleotide selected from the group consisting of adenosine, guanosine, cytidine and uridine.

Alternatively, the RNA microhelix can comprise a structure selected from the group consisting of

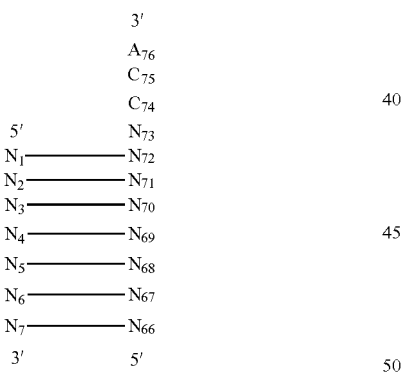

(SEQ ID NO.: 2),

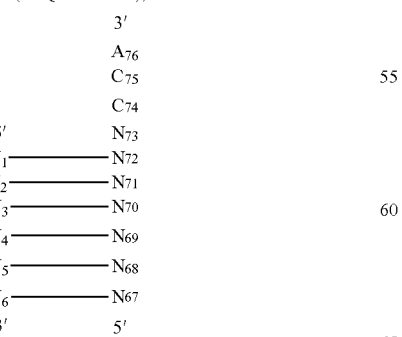

(residues 2-11 of (SEQ ID NO.: 2),

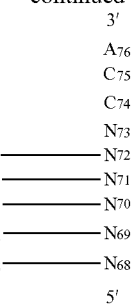

(residues 3-11 of (SEQ ID NO.: 2), and

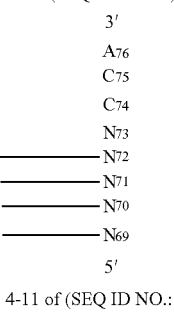

(residues 4-11 of (SEQ ID NO.: 2), wherein each N independently is a ribonucleotide selected from the group consisting of adenosine, guanosine, uridine and cytidine. The horizontal lines represent one or more optional bonds, for example, hydrogen bonds, between a pair of ribonucleotides, for example, a Watson and Crick-type base pair. For illustrative purposes, in the case of a Watson and Crick-type base pair, if $N_1$ is an adenosine or uridine, then $N_{72}$ optionally is a uridine or adenosine, respectively, wherein $N_1$ is hydrogen bonded to $N_{72}$.

Alternatively, the RNA microhelix can comprise a structure selected from the group consisting of

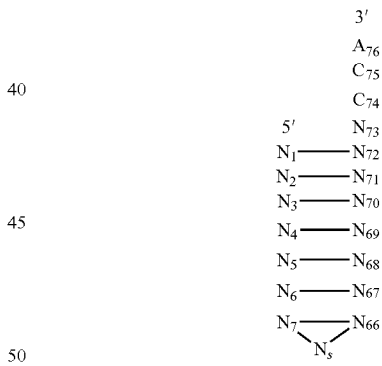

(SEQ ID NO.: 3),

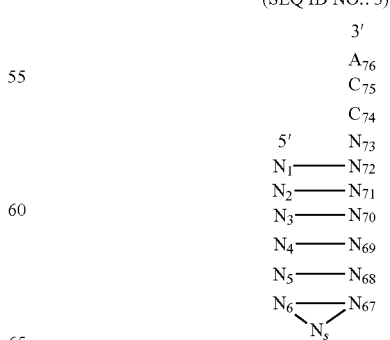

(SEQ ID NO.: 4),

-continued

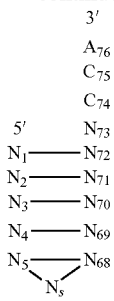

(SEQ ID NO.: 5), and

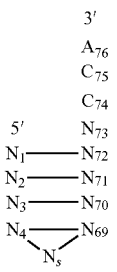

(SEQ ID NO.: 6), wherein s=2, 3, 4, 5, 6, or 7, and each N independently is a ribonucleotide selected from the group consisting of adenosine, guanosine, uridine and cytidine. The horizontal lines represent one or more optional bonds, for example, hydrogen bonds, between a pair of ribonucleotides, for example, a Watson and Crick-type base pair. For illustrative purposes, in the case of a Watson and Crick-type base pair, if $N_1$ is an adenosine or uridine, then $N_{72}$ optionally is a uridine or adenosine, respectively, wherein $N_1$ is hydrogen bonded to $N_{72}$.

Alternatively, the RNA microhelix can comprise the structure

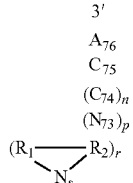

(SEQ ID NO.: 7)

wherein, each N independently is a ribonucleotide selected from the group consisting of adenosine, guanosine, uridine and cytosine, $R_1$ and $R_2$ is a pair of based paired ribonucleotides selected from the group consisting of adenosine-uridine, uridine-adenosine, guanosine-cytidine and cytidine-guanosine, n=0 or 1, p=0 or 1, r=0 or 1, 2, 3, 4, 5, 6, or 7 and s=0 or 2, 3, 4, 5, 6, or 7, provided that when r=0, s=0.

Alternatively, the RNA microhelix can comprise the structure

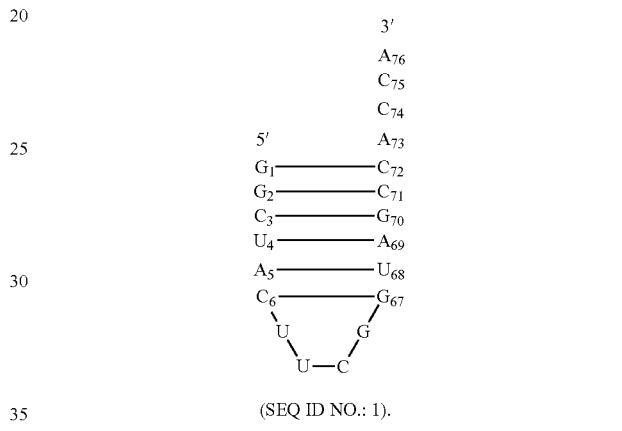

(SEQ ID NO.: 1).

Alternatively, the RNA microhelix can comprise the structure

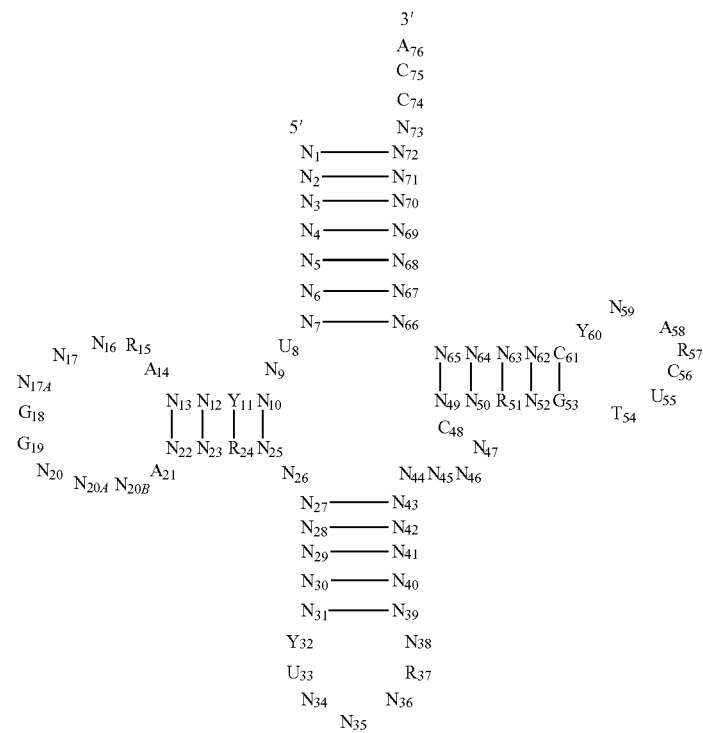

(SEQ ID NO.: 8), wherein each N independently is any ribonucleotide (adenosine, guanosine, uridine or cytidine), R is adenosine or guanosine, Y is uridine or cytidine, T is ribothymidine, and N—N optionally is a Watson and Crick-type base pair. Residues $N_1$-$N_7$ and $N_{66}$-$A_{76}$ collectively define the acceptor-stem, residues $U_8$-$N_{26}$ collectively define the D stem-loop, residues $N_{27}$-$N_{43}$ collectively define the anticodon stem-loop (wherein residues $N_{34}$, $N_{35}$ and $N_{36}$ define the anticodon sequence), and residues N44-N65 collectively define the T stem-loop. The horizontal and vertical lines represent one or more optional bonds, for example, hydrogen bonds, between a pair of ribonucleotides, for example, a Watson and Crick-type base pair. For illustrative purposes, in the case of a Watson and Crick-type base pair, if $N_1$ is an adenosine or uridine, then $N_{72}$ optionally is a uridine or adenosine, respectively, wherein $N_1$ is hydrogen bonded to $N_{72}$ The atomic co-ordinates of residues defining the microhelix binding site can comprise those residues conserved between ribosomes or ribosomal subunits of pathogens, for example, prokaryotic organisms, but, optionally are also absent from ribosomes or ribosomal subunits of a host organism, for example, a mammal, for example, a human. The structures provided herein can be used in rational design of candidate molecules, for example, analogs or derivatives of the RNA microhelix, that disrupt protein biosynthesis in a pathogen, for example, a bacteria, but optionally and preferentially do not disrupt or otherwise substantially affect protein synthesis in a host organism, for example, a human.

The atomic co-ordinates defining the RNA microhelix in the computer system can comprise at least a portion of the atomic co-ordinates recorded on Disk No. 1 under file name microhelix.pdb or microhelixa.pdb, or may be produced by molecular modeling as discussed herein.

In addition, the invention provides a computer system comprising: (a) a memory having stored therein data indicative of atomic co-ordinates defining at least a portion of an RNA microhelix when the microhelix is in association with a microhelix binding site of a large subunit of a ribosome; and (b) a processor in electrical communication with the memory, the processor comprising a program for generating a three-dimensional model representative of at least a portion of the microhelix. The computer system optionally further comprises a device, for example, a computer monitor or terminal, for providing a visual representation of the molecular model. The processor optionally further comprises one or more programs to facilitate rational drug design.

The atomic coordinates of two examples of RNA microhelices in association with the large ribosomal subunit, i.e. two RNA microhelix-ribosome complexes of the present invention, are provided herein. In one instance the atomic co-ordinates defining the three-dimensional structure of the RNA microhelix of Formula I in the presence of the large ribosomal subunit are recorded on compact disk, Disk No. 1, under file name microhelix.pdb. In another instance the atomic co-ordinates defining the three-dimensional structure of the RNA microhelix of Formula II and the three-dimensional structure of the large ribosomal subunit defining the microhelix site are recorded on compact disk, Disk No. 1, under file name microhelixa.pdb. Also, a set of atomic co-ordinates defining the three-dimensional structure of the large ribosomal subunit resolved in the absence of a RNA microhelix are recorded on compact disk, Disk No. 1, under file name 1JJ2.pdb.

The skilled artisan, using the atomic co-ordinates provided herein, can generate models of a ribosomal subunit of interest using conventional molecular modeling techniques including, for example, homology modeling and/or molecular replacement techniques. The models can then be used for the rational design of candidate molecules that are protein synthesis modulators.

The atomic co-ordinates optionally are used to produce a molecular model in an electronic form. The atomic co-ordinates represent the three-dimensional structure of the RNA microhelix in a bound state within the ribosome, which can differ from the structure of the microhelix when free in solution. The RNA microhelix binding site of the large ribosomal subunit is defined by a plurality of residues set forth in Table 1 or Table 2. From the studies described herein, it appears that the conformation of certain residues of the large ribosomal subunit that define both the microhelix binding site and the E-site (namely residues Lys-54, Val-55, Pro-56, Gly-57 and Gly-58 present in protein L44E) undergo a conformational change or change location upon binding of an RNA microhelix.

In another aspect, the invention provides a variety of methods for designing, testing and refining new candidate molecules by rational drug design. For example, the invention provides a method of identifying a molecule that binds to a large ribosomal subunit. The method comprises the steps of: (a) providing a molecular model of at least a portion of a RNA microhelix binding site of a large subunit of a ribosome; and (b) using the molecular model to identify a candidate molecule capable of binding to at least a portion of the RNA microhelix binding site of molecular model. In step (a), the molecular model can be created, for example, from (i) the atomic co-ordinates for the *Haloarcula marismortui* large ribosomal subunit found on Disk 1 under file name microhelix.pdb or microhelixa.pdb, or (ii) atomic co-ordinates derived by molecular modeling from the *Haloarcula marismortui* atomic co-ordinates found on Disk 1 under file name microhelix.pdb or microhelixa.pdb.

In the method, the candidate molecule binds specifically to the RNA microhelix binding site of the molecular model. The candidate molecule preferably defines a molecular surface that is spatially and/or chemically complementary to the RNA microhelix binding site, and more preferably interfits stereochemically with the RNA microhelix binding site of the molecular model.

The molecular model provided in step (a) can be generated by molecular modeling, for example, by homology modeling or molecular replacement. Furthermore, the molecular model may be in electronic form. In addition, the molecular model provided in step (a) optionally comprises residues of the large ribosomal subunit that are conserved among one or more prokaryotic organisms.

The method optionally further comprises one or more additional steps of: producing the candidate molecule identified in step (b); determining whether the candidate molecule modulates (for example, induces or reduces) ribosomal activity; identifying a modified candidate molecule (i.e., a molecule that differs by at least one atom from the candidate molecule or that is an isomer of the candidate molecule); producing the modified candidate molecule; determining whether the modified candidate molecule, when produced, modulates ribosomal activity; and producing the modified candidate molecule in commercially reasonable amounts for use either alone or in combination with a pharmaceutically acceptable carrier or excipient. The candidate molecule and/or the modified candidate molecule preferably is an antibiotic, at least a portion of which binds the E-site of the large ribosomal subunit.

The atomic co-ordinates optionally are used to produce a molecular model in an electronic form. The atomic co-ordinates provided herein, can generate models of a molecule of interest using conventional molecular modeling techniques including, for example, conventional homology modeling and/or molecular replacement techniques. The models can then be used for the rational design of analogs and/or derivatives of the RNA microhelices.

In another aspect, the invention provides a method of identifying a candidate molecule. The method comprises the steps of: (a) providing a molecular model of at least a portion of an RNA microhelix molecule when bound to at least a portion of an RNA microhelix binding site of a large subunit of a ribosome; (b) using the molecular model identifying a candidate molecule capable of binding to the RNA microhelix binding site; and (c) producing the candidate molecule produced in step (b). The candidate molecule preferably defines a molecular surface that is spatially and/or chemically complementary to the RNA microhelix binding site, and more preferably interfits stereochemically with the microhelix binding site of the large ribosomal subunit.

The method optionally further comprises one or more additional steps of: determining whether the candidate molecule modulates (for example, induces or reduces) ribosomal activity; identifying a modified candidate molecule (i.e., a molecule that differs by at least one atom from the candidate molecule or that is an isomer of the candidate molecule); producing the modified candidate molecule; determining whether the modified candidate molecule, when produced, modulates ribosomal activity. These steps can be repeated one or more times until a modified candidate molecule having the desired biological activity and/or pharmacokinetic properties. Once such a compound has been designed, synthesized and tested for activity, it can then be produced in commercially reasonable amounts for use as a pharmaceutical, for example, when formulated with a pharmaceutically acceptable carrier or excipient. The candidate molecule and/or the modified candidate molecule preferably is an antibiotic at least a portion of which binds the E-site of the large ribosomal subunit.

The foregoing aspects and embodiments of the invention can be more fully understood by reference to the following figures, detailed description and claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The objects and features of the invention can be more fully understood by reference to the drawings described below in which.

DETAILED DESCRIPTION OF THE INVENTION

I. Definitions

Figure 1:
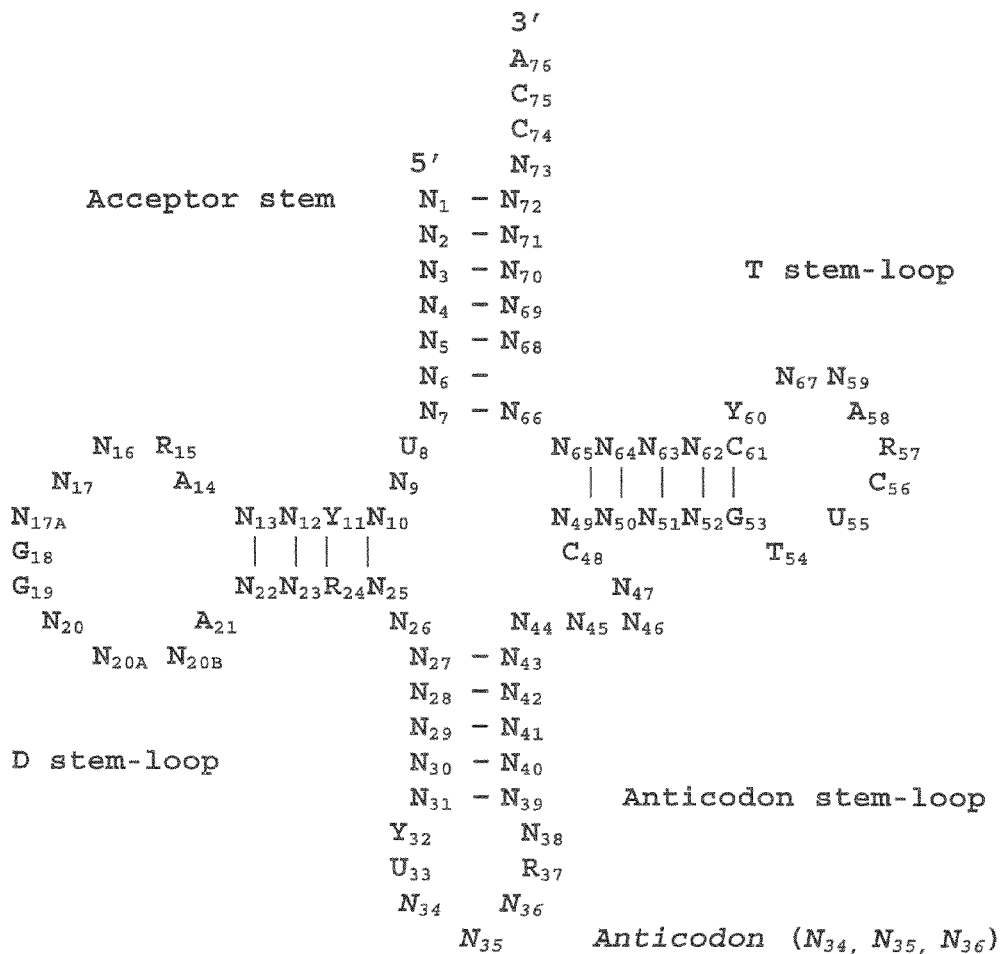
FIG. 1 is a pictorial representation of a tRNA molecule.

As used herein, the term "RNA microhelix," which can also be referred to as "RNA minihelix," refers to an RNA molecule (i) which associates with or binds to a large ribosomal subunit, and (ii) when associated with or bound to the large ribosomal subunit comprises one or more ribonucleotides, one or more atoms of which are located within 12.6 Å (atom center to atom center), more preferably 5.8 Å (atom center to atom center) from atoms of the residues set forth in Table 1. The RNA microhelix lacks an amino acid coupled to its 3' end and, therefore, can be considered to mimic a deacylated tRNA molecule. By way of example, the RNA microhelix can comprise, for example, a molecule having the structure set forth below in Formula III

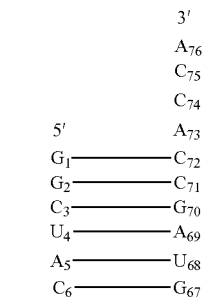

Formula III (residues 11-20 of SEQ ID NO.: 1), wherein, residues $G_1$, $G_2$, $C_3$, $U_4$, $A_{69}$, $G_{70}$, $C_{71}$, $C_{72}$, $A_{73}$, $C_{74}$, $C_{75}$ and $A_{76}$ represent core residues, and $C_6$— $G_{67}$ optionally are further linked together by a ribonucleotide linker comprising, for example,

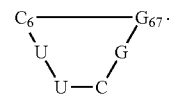

As used herein, the term "candidate molecule" refers to (i) a molecule, for example, an analog or derivative of an RNA microhelix, which binds to at least a portion of the RNA microhelix binding site defined by the residues of Table 1 and/or (ii) a molecule having at least 15 non-hydrogen atoms having an r.m.s. deviation of less than 2.0 Å when superpositioned with the corresponding non-hydrogen atoms of the RNA microhelix of Formula III, when disposed in the RNA microhelix binding site, as determined using the molecular modeling system MIDAS Plus.

As used herein, the term "RNA microhelix binding site" refers to the ribofunctional locus of the large ribosomal subunit occupied by the RNA microhelix of Formula III. The RNA microhelix binding site defines at least a portion of or overlaps with the E-site.

As used herein, the term "A-site" refers to the ribofunctional locus occupied by an aminoacyl-tRNA molecule immediately prior to its participation in the peptide-bond forming reaction.

As used herein, the term "E-site" refers to the ribofunctional locus occupied by a deacylated tRNA molecule following its participation in the peptide-bond forming reaction.

As used herein, the term "P-site" refers to the ribofunctional locus occupied by a peptidyl-tRNA at the time it participates in the peptide-bond forming reaction.

As used herein and in reference to a ribosome or ribosomal subunit, the terms "a portion of" or "a portion of the three-dimensional structure of" are understood to mean a portion of the three-dimensional structure of a ribosome or ribosomal subunit, including charge distribution and hydrophilicity/hydrophobicity characteristics, formed by at least three, more preferably at least three to ten, and most preferably at least ten amino acid residues and/or nucleotide residues of the ribosome or ribosomal subunit. The residues forming such a portion can be, for example, (i) contiguous residues based upon, for example, a primary sequence of a ribosomal RNA or ribosomal protein, (ii) residues which form a contiguous portion of the three-dimensional structure of the ribosome or ribosomal subunit, or (c) a combination thereof. As used herein and in reference to the RNA microhelix, the terms "a portion of" or "a portion of the three-dimensional structure of" are understood to mean a portion of the three-dimensional structure of RNA microhelix, including charge distribution and hydrophilicity/hydrophobicity characteristics, formed by at least three, more preferably at least three to ten atoms of one or more core residues of Formula III. The atoms forming such a portion can be, for example, (i) solvent inaccessible atoms buried within the core of the RNA microhelix, (ii) solvent accessible atoms of the RNA microhelix, or (iii) a combination thereof.

With regard to the list of atomic co-ordinates recorded on Disk 1, the term "atomic co-ordinate" or "structure co-ordinates" refer to the measured position of an atom in the structure in Protein Data Bank (PDB) format, including X, Y, Z and B, for each. The term "atom type" refers to the element whose co-ordinates are measured. The first letter in the column defines the element. The term "X", "Y", "Z" refers to the crystallographically defined atomic position of the element measured with respect to the chosen crystallographic origin. The term "B" refers to a thermal factor that measures the mean variation of an atom's position with respect to its average position. The atomic co-ordinates recorded on Disk 1, are recorded in PDB format. For purposes of exemplification only, in the file 1JJ2.pdb recorded on Disk 1, the "X", "Y", and "Z" values for atom 1 (an oxygen atom) include "16.071", "148.494", and "104.415", respectively and the thermal factor for atom 1 is "83.83".

Reference is made to the sets of atomic co-ordinates and related tables included with this specification and submitted on compact disk (two total compact disks including one original compact disk, and a duplicate copy of the original compact disk). As will be apparent to those of ordinary skill in the art, the atomic structures presented herein are independent of their orientation, and that the atomic co-ordinates identified herein merely represent one possible orientation of the molecule of interest. It is apparent, therefore, that the atomic co-ordinates identified herein can be mathematically rotated, translated, scaled, or a combination thereof, without changing the relative positions of atoms or features of the respective structure. Such mathematical manipulations are intended to be embraced herein. Those of skill in the art understand that a set of structure co-ordinates determined by X-ray crystallography is not without standard error.

The structures of two ribosomes, ribosomal subunits or portions thereof are considered to be the same if they satisfy one of the following two tests. In a first test, the structures are considered to be the same if a set of structure co-ordinates for a ribosome, ribosomal subunit or a portion of a large ribosomal subunit from any source has a root mean square (r.m.s.) deviation as determined by MIDAS Plus of non-hydrogen atoms of less than about 2.0 Å, or more preferably less than about 0.75 Å, when superimposed on the corresponding non-hydrogen atom positions of the atomic co-ordinates recorded on compact disk, Disk No. 1 under file name 1JJ2.pdb. In a second test, the structures are considered to be the same if the r.m.s. deviation between a set of atoms in a test structure and a corresponding set of atoms in a reference structure is less than 2.0 Å. For the purposes of this test, the set of atoms in the reference structure comprises (i) at least five of the series of 23S rRNA residues listed below as 631-633, 835-841, 844-846, 882-885, 1836-1839, 2095-2105, 2474-2478, 2485-2490, 2528-2530, 2532-2543, 2607-2612, 2614-2623, 2642-2648 of the residues of the large ribosomal subunit structure recorded on compact disk, Disk No. 1 under file name 1JJ2.pdb, (ii) at least five atoms of residues of the large ribosomal subunit structure recorded on compact disk, Disk No. 1, under the file name microhelix.pdb that are located within 5.8 Å (atom center to atom center) of the atoms defining the microhelix structure recorded on compact disk, Disk No. 1, under file name microhelix.pdb, or (iii) at least five atoms of residues of the large ribosomal subunit structure recorded on compact disk, Disk No. 1, under the file name microhelixa.pdb that are located within 5.8 Å (atom center to atom center) of the atoms defining the microhelix structure recorded on compact disk, Disk No. 1, under file name microhelixa.pdb.

The residues in the test structure corresponding to the ones listed above are identified by sequence alignment using the program Lasergene v. 5.0 (DNA Star, Inc., Madison, Wis.) with the default settings. For example, the computer program is used to align those residues listed above in the *Haloarcula marismortui* 23S rRNA sequence with those in the test organism's rRNA. Once aligned, the corresponding residues in the test organism's rRNA are identified. The atomic co-ordinates of backbone atoms (P, C5', C5', C4', C3', C3') in the test structure are superimposed upon the corresponding backbone atoms (P, C5', C5', C4', C3', C3') of the reference structure using the program MIDAS Plus (Ferrin et al. (1988) *J. Mol. Graphics.* 6: 13-27 and 36-37). The test and reference structures are considered the same if the r.m.s. deviation between the two sets of atoms after superpositioning is less than 2.0 Å, as determined by MIDAS Plus.

The structures of two RNA microhelix molecules or portions thereof are considered to be the same if the r.m.s. deviation between the atomic co-ordinates of at least 15 atoms of a test structure are within 2.0 Å, as determined by MIDAS Plus, of the corresponding non-hydrogen atoms set forth in the RNA microhelix reference structure (as included in file names microhelix.pdb and microhelixa.pdb recorded on compact disk, Disk No. 1).

As used herein, the terms "atoms derived from," "atomic co-ordinates derived from," and "atomic co-ordinates derived by molecular modeling from" refer to atoms or atomic co-ordinates derived from at least a portion of the atoms recorded on Disk 1. It is understood that atoms or atomic co-ordinates found, present or recorded on Disk 1 are considered to be primary atoms or atomic co-ordinates. It is understood that atoms or atomic co-ordinates derived from the atoms recorded on Disk 1 are considered to be derivatives or transforms of the atoms or atomic co-ordinates recorded on Disk 1, i.e. are considered to be secondary atoms or atomic co-ordinates. The secondary atoms or atomic co-ordinates may be generated from the primary atoms or atomic co-ordinates by using conventional molecular modeling techniques. By way of a non limiting example, the atomic co-ordinates for the *H. marismortui* large ribosomal subunit as described herein are considered to be primary co-ordinates, whereas the atomic co-ordinates of a mammalian large ribosomal subunit which are derived from *H. marismortui* atomic co-ordinates by molecular modeling, including, for example, homology modeling and/or molecular replacement, are considered to be secondary co-ordinates.

As used herein the terms "bind," "binding," or "bound" when used in reference to the association of molecules or chemical groups refer to any physical contact or association of two or more atoms, molecules, or chemical groups (e.g., the binding of a candidate molecule with a ribosomal subunit refers to the physical contact between the candidate molecule and the ribosomal subunit). Such contacts and associations include covalent and non-covalent types of interactions.

As used herein, the term "pharmaceutically acceptable salt, ester or prodrug thereof" refers to salt, ester, or prodrug derivatives of the compound of interest. By "pharmaceutically acceptable" is meant a salt, ester, or prodrug of the compound of interest that is generally intended as a safe and nontoxic modification as understood by one of ordinary skill in the art. One of ordinary skill in the art can generally prepare a pharmaceutically acceptable salt, ester or prodrug of a compound of interest using standard chemical techniques. A pharmaceutically acceptable salt is where the compound of interest is modified by making an acid or base salt thereof. A pharmaceutically acceptable ester is where a hydroxyl group of the compound of interest, if present, is esterified to make an ester, i.e., typically a simple ester such as a methyl or ethyl ester or the like. A pharmaceutically acceptable prodrug is where a functional group of the compound of interest is modified, typically to alter the physical characteristics of the compound of interest for formulation, drug delivery, or other such purposes. An example of a prodrug would be an acetamide derivative of an amine containing drug.

As used herein, the term "ribofunctional locus" refers to a region of the ribosome or ribosomal subunit that participates, either actively or passively, in protein or polypeptide synthesis within the ribosome or ribosomal subunit and/or export or translocation of a protein or polypeptide out of a ribosome. The ribofunctional locus can include, for example, a portion of a peptidyl transferase-site, an A-site, a P-site, an E-site, an elongation factor binding domain, a polypeptide exit tunnel, a signal recognition particle (SRP) binding domain, or an antibiotic binding site. It is understood that the ribofunctional locus will not only have a certain topology but also a particular surface chemistry defined by atoms that, for example, participate in hydrogen bonding (for example, proton donors and/or acceptors), have specific electrostatic properties and/or hydrophilic or hydrophobic character.

As used herein, the term "ribosomal subunit" refers to one of the two subunits of the ribosome that can function independently during the initiation phase of protein synthesis but which both together constitute a ribosome. The ribosomes of all species comprise a one to one complex of two subunits of unequal size, the larger typically being about twice the molecular weight of the smaller. For example, a prokaryotic ribosome comprises a 50S subunit (large ribosomal subunit) and a 30S subunit (small ribosomal subunit).

II. Structure of a RNA Microhelix in Association with a Large Ribosomal Subunit and Uses Thereof A. Three-Dimensional Structure of an RNA Microhelix The present invention is based, in part, upon the three-dimensional structure of a RNA microhelix when associated with the large ribosomal subunit. The RNA microhelix is a mimetic of a deacylated tRNA molecule when still bound to the ribosome after having donated its amino acid to the polypeptide chain being synthesized at the peptidyl transferase site. As a result, the RNA microhelix defines at least a portion of the heretofore unknown E-site. Crystals of the *H. marismortui* large ribosomal subunit were soaked with a RNA microhelix at a concentration of about 5 mM (which is equivalent to about 3% w/w for the polynucleotide of Formula I, or about 0.5% w/w for the polynucleotide of Formula II). The structure of the large ribosome subunit complexed with the RNA microhelix was resolved via X-ray diffraction studies.

Briefly, a small amount of a concentrated RNA microhelix solution was added to a large subunit crystal suspended in stabilization solution and incubated overnight. Following freezing and the other procedures normally used to prepare such crystals for experimental use, X-ray diffraction data were collected from the RNA microhelix containing crystals. Because the crystals were isomorphous with crystals already described (see, for example, U.S. Patent Application Publication No. US 2002/0086308 A1, published Jul. 4, 2002), the phases obtained for native crystal were combined with the diffraction intensities obtained from the RNA microhelix-soaked crystal to obtain a structure for the latter. The position of the RNA microhelix in the crystal was revealed most clearly in difference electron density maps, which are electron density maps computed using the phases just referred to and amplitudes obtained by subtracting the amplitudes of crystals that contain no RNA microhelix from the (suitably scaled) amplitudes of those that contain the RNA microhelix. By using the foregoing methods, it was possible to determine the atomic co-ordinates that show the spatial relationship between the RNA microhelix and its binding site within the large ribosomal subunit.

The atomic co-ordinates of the large ribosomal subunit when associated with an RNA microhelix of Formula I are recorded on compact disk, on Disk No. 1 under the file name microhelix.pdb. The atomic co-ordinates of the large ribosomal subunit when associated with an RNA microhelix of Formula II are recorded on compact disk, on Disk No. 1 under the file name microhelixa.pdb.

Figure 2:
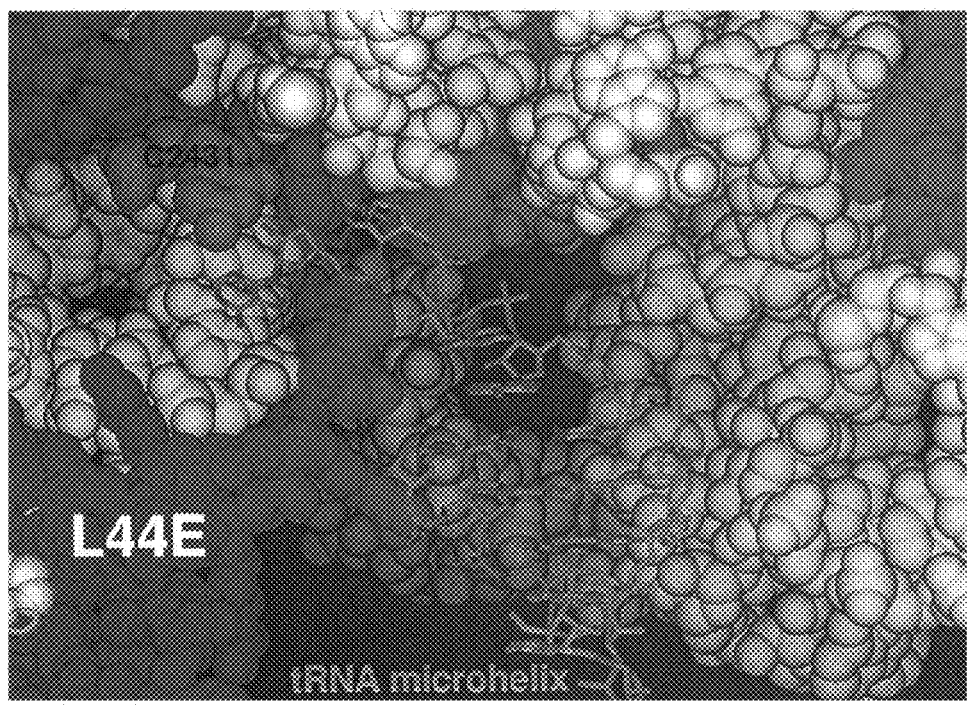
FIG. 2 is a pictorial representation showing the spatial relationship between the RNA microhelix of Formula I when bound to a large ribosomal subunit.
Figure 3:
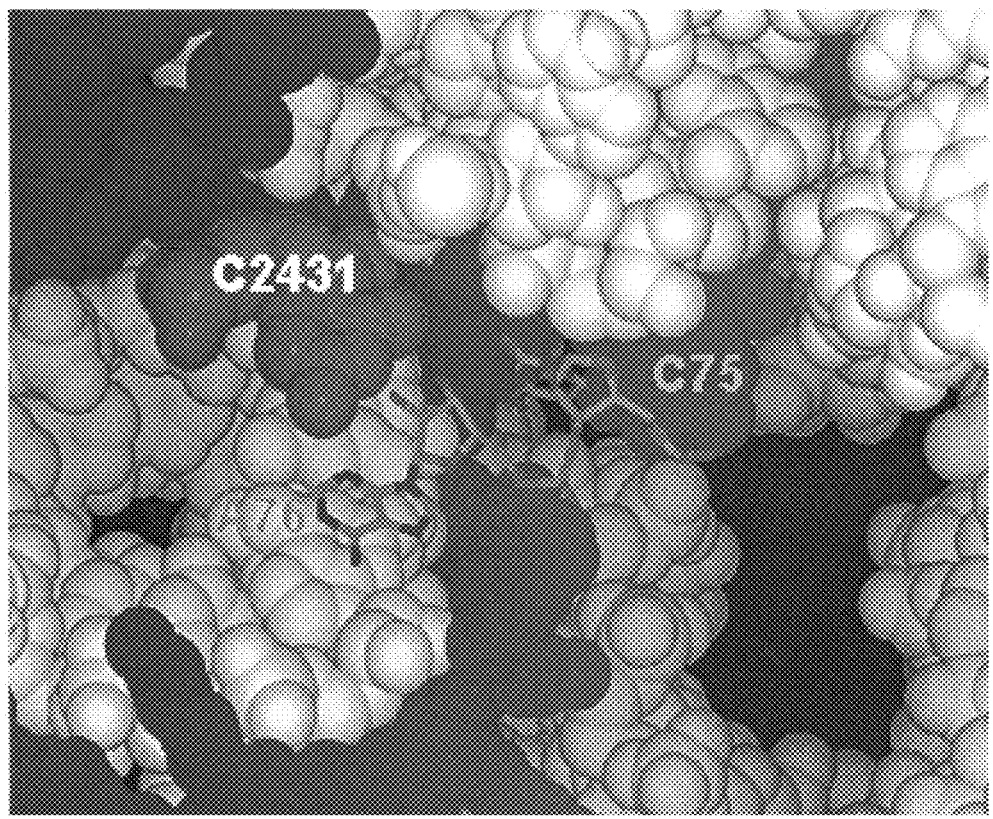
FIG. 3 is a pictorial representation showing the spatial relationship between the RNA microhelix of Formula II when bound to a large ribosomal subunit.

In one embodiment, the RNA microhelix binding site includes, without limitation, a plurality (e.g., at least three) of the residues including, for example, one or more of the residues listed in Table 1. In another embodiment, the RNA microhelix binding site includes, without limitation, a plurality (e.g., at least three) of the residues including, for example, one or more of the residues listed in Table 2. In addition, FIG. 2 shows the spatial relationship between the RNA microhelix and the large ribosomal subunit, when the RNA microhelix of Formula I is disposed therein, or otherwise associated with, the large ribosomal subunit, and FIG. 3 shows the spatial relationship between the RNA microhelix and the large ribosomal subunit, when the RNA microhelix of Formula II is disposed therein, or otherwise associated with, the large ribosomal subunit.

Based on these studies, it is possible to make several observations concerning the binding of the RNA microhelix to the large ribosomal subunit. The RNA microhelix binding site on the large ribosomal subunit is bipartite. Approximately, one half of the binding site interacts with the last two residues at the 3'-terminus of the microhelix, namely C75 and A76. These two residues are unstacked from the remainder of the microhelix, and make extensive contacts with a small pocket in the large ribosomal subunit. There are interactions between the 2' OH and 3' OH of A76, which are recognized primarily by the universally conserved 23S RNA residue C2431. The geometry of these interactions ensures that the large ribosomal E-site binds deacylated tRNA, in accordance with biochemical observations of ribosomal function. Interactions are also seen between microhelix residues C75, A76 and a portion of protein L44E, namely residues 54-58, which move to accommodate these microhelix residues. The second, spatially separated half of the binding site, primarily 23S RNA residues 1932-1934 and 1905-1908, binds to a distinct portion of the microhelix of Formula I, namely residues 2-4 and 70-72. It should be noted, however, that a smaller microhelix, such as the microhelix of Formula II, does not interact with the second half of the spatially separate 23 S RNA residues 1932-1934 and 1905-1908.

It is contemplated that the atomic co-ordinates for the residues described herein and homologs thereof may be useful in rational drug design to identify candidate molecules that bind to a microhelix binding site or at least a portion of the E-site of the ribosome and modulate ribosomal function. In particular, based on the foregoing studies, it has been discovered that at least one amino acid residue selected from the group consisting of Lysine-54, Valine-55, Proline-56, Glycine-57, and Glycine-58 present in *Haloarcula marismortui* ribosomal protein L44E move to accommodate the binding of a microhelix. It is contemplated that the same or corresponding amino acid residues present in homologs of the *Haloarcula* L44E protein (i.e., proteins having at least 55%, more preferably at least 75%, more preferably at least 85%, and most preferably at least 95% sequence identity with *Haloarcula marismortui* ribosomal protein L44E) may also move to accommodate the binding of a microhelix. This information can be used to create candidate molecules that interact with one or more amino acid side chains in L44E.

In order to determine whether a particular ribosomal protein has the requisite percentage identity to *Haloarcula marismortui* L44E (i.e., is a homolog of L44E), the candidate amino acid sequence and the reference L44E amino acid sequence are first aligned using the dynamic programming algorithm described in Smith and Waterman (1981) *J. Mol. Biol.* 147:195-197, in combination with the BLOSUM62 substitution matrix described in FIG. 2 of Henikoff and Henikoff (1992) *Proc. Natl. Acad. Sci. USA* 89:10915-10919. For purposes of this invention, an appropriate value for the gap insertion penalty is −12, and an appropriate value for the gap extension penalty is −4. Computer programs performing alignments using the algorithm of Smith-Waterman and the BLOSUM62 matrix, such as the GCG program suite (Oxford Molecular Group, Oxford, England), are commercially available and widely used by those skilled in the art.

Once the alignment between the candidate and reference L44E sequence has been made, a percent identity may then be calculated. In order to calculate a percent identity, the aligned amino acids of each sequence are compared sequentially. If the amino acids are non-identical, the pairwise identity score is zero; otherwise the pairwise identity score is 1.0. The raw identity score is the sum of the identical aligned amino acids. The raw score is then normalized by dividing it by the number of amino acids in the smaller of the candidate or reference sequences. The normalized raw score is the percent identity. Insertions and deletions are ignored for the purposes of calculating percent identity. Accordingly, gap penalties are not used in this calculation, although they are used in the initial alignment.

B. Rational Drug Design

1. Introduction

The atomic co-ordinates defining the three-dimensional structure of at least a portion of RNA microhelix, when associated with a large ribosomal subunit, can be used in rational drug design (RDD) to design a novel molecule of interest, for example, a novel modulator (for example, inducer, mimetic or inhibitor) of ribosome function. Furthermore, it is contemplated that, by using the principles disclosed herein, the skilled artisan can design, make, test, refine and use analogs specifically engineered to reduce, disrupt, or otherwise or inhibit ribosomal function in an organism or species of interest. For example, by using the principles discussed herein, the skilled artisan can engineer new molecules that specifically target and inhibit ribosomal function in a pathogen, for example, a particular prokaryotic, organism, while preserving ribosomal function in a host, for example, a eukaryotic organism, specifically a mammal, and more specifically, a human. As a result, the atomic co-ordinates provided herein permit the skilled artisan to design new antibiotics that can kill certain pathogenic organisms while having little or no toxicity in the intended recipient, for example, a human.

It is contemplated that RDD using atomic co-ordinates of the large ribosomal subunit can be facilitated most readily via computer-assisted drug design (CADD) using conventional computer hardware and software known in the art. The candidate molecules can be designed de novo or can be designed as a modified version of an already existing molecule, for example, a pre-existing antibiotic or protein synthesis modulator, using conventional methodologies. Once designed, candidate molecules can be synthesized using standard methodologies known in the art. Following synthesis, the candidate molecules can be screened for bioactivity, for example, their ability to interact with or bind specifically to a ribosome or a ribosomal subunit, or by their ability to reduce or inhibit ribosome function. Based in part upon these results, the candidate molecules can be refined iteratively using one or more of the foregoing steps to produce a more desirable molecule with a desired biological activity. The processes can be repeated as many times as necessary to obtain molecules with desirable binding properties and/or biological activities. The resulting molecules can be useful in treating, inhibiting or preventing the biological activities of target organisms, thereby killing the organism or impeding its growth. Alternatively, the resulting molecules can be useful for treating, inhibiting or preventing microbial infections in any organism, particularly animals, more particularly humans.

2. Identification of Candidate Molecules

It is contemplated that the design of candidate molecules of interest can be facilitated by conventional ball and stick-type modeling procedures. However, in view of the size and complexity of the molecules of interest when associated with a large ribosomal subunit, it is contemplated that the ability to design candidate molecules can be enhanced significantly using computer-based modeling and design protocols.

a. Molecular Modeling

It is contemplated that the design of candidate molecules, as discussed in detail hereinbelow, can be facilitated using conventional computers or workstations, available commercially from, for example, Silicon Graphics Inc. and Sun Microsystems, running, for example, UNIX based, Windows NT on IBM OS/2 operating systems, and capable of running conventional computer programs for molecular modeling and rational drug design.

Figure 4:
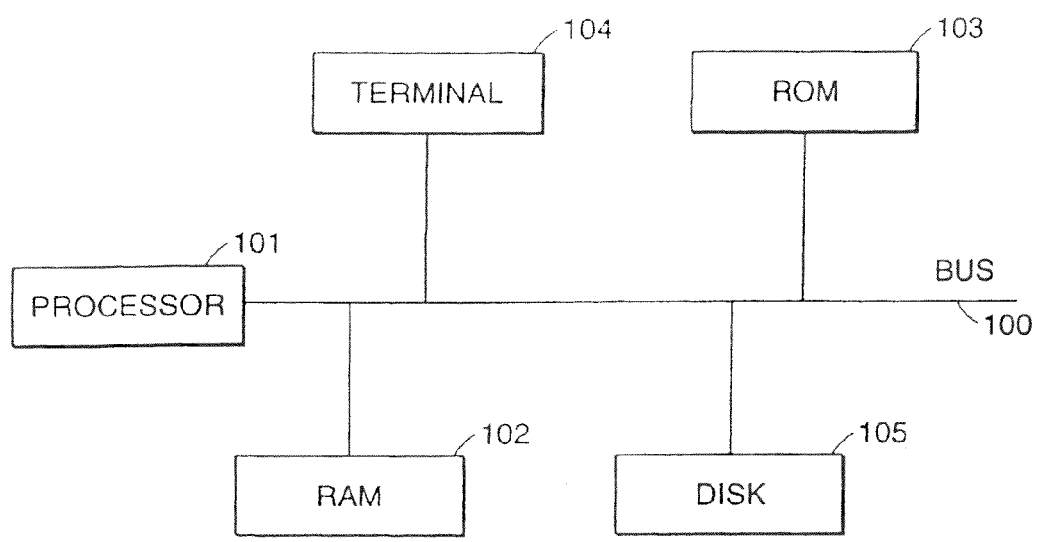
FIG. 4 is a schematic representation of a computer system useful in molecular modeling a ribosomal subunit and/or for performing rational drug design.

It is understood that any computer system having the overall characteristics set forth in FIG. 4 can be useful in the practice of the invention. More specifically, FIG. 4, is a schematic representation of a typical computer work station having in electrical communication (100) with one another via, for example, an internal bus or external network, a central processing unit (101), a random access memory (RAM) (102), a read only memory (ROM) (103), a monitor or terminal (104), and optionally an external storage device, for example, a diskette, CD ROM, or magnetic tape (105).

The terms "computer system" or "computer-based system" refer to hardware, software, and data storage devices capable of, for example, storing, analyzing, manipulating and/or presenting the atomic co-ordinates of the invention. The data storage device can be any memory device which can store data indicative of atomic co-ordinates.

The data indicative of atomic co-ordinates can be recorded on computer readable medium including, for example, any medium which can be read and accessed directly by a computer. Such media include, but are not limited to: magnetic storage media, such as floppy discs, hard disc storage medium, and magnetic tape; optical storage media such as optical discs or CD-ROMs; electrical storage media such as RAM and ROM; and hybrids of these categories such as magnetic/optical storage media. A skilled artisan can readily appreciate how any of the presently known computer readable media can be used to create a manufacture comprising computer readable medium having recorded thereon data indicative of the atomic co-ordinates of the invention. A skilled artisan can readily adopt any of the presently known methods for recording information on computer readable medium to generate manufactures comprising data indicative of atomic co-ordinates of the invention.

A variety of data storage structures are available to a skilled artisan for creating a computer readable medium having recorded thereon data indicative of atomic co-ordinates of the invention. The choice of the data storage structure will generally be based on the means chosen to access the stored information. In addition, a variety of data processor programs and formats can be used to store the atomic co-ordinates of the present invention on computer readable medium. The foregoing data can be represented in a word processing text file, formatted in commercially-available software such as WordPerfect and MICROSOFT Word, or represented in the form of an ASCII file, stored in a database application, such as DB2, Sybase, Oracle, or the like. A skilled artisan can readily adapt any number of data processor structuring formats (e.g. text file or database) in order to obtain computer readable medium having recorded thereon the information of the present invention.

By providing a computer readable medium having stored therein data indicative of atomic co-ordinates, a skilled artisan can routinely access the data to model the protein synthesis modulator of interest or derivatives or analogs thereof, either alone or in combination with a ribosome or ribosomal subunit. Computer algorithms are publicly and commercially available which allow a skilled artisan to access this data provided in a computer readable medium and analyze it for molecular modeling and/or RDD. See, e.g., *Biotechnology Software Directory*, MaryAnn Liebert Publ., New York, N.Y. (1995).

Although computers are not required, molecular modeling can be most readily facilitated by using computers to build realistic models of the protein synthesis modulator or analogs thereof, either or alone or in combination with a ribosome or ribosomal subunit. The methods utilized in molecular modeling range from molecular graphics (i.e., three-dimensional representations) to computational chemistry (i.e., calculations of the physical and chemical properties) to make predictions about the binding of the smaller molecules or their activities; to design new molecules; and to predict novel molecules, including ligands such as drugs, for chemical synthesis.

For basic information on molecular modeling, see, for example, M. Schlecht, *Molecular Modeling on the PC* (1998) John Wiley & Sons; Gans et al., *Fundamental Principals of Molecular Modeling* (1996) Plenum Pub. Corp.; N.C. Cohen, ed., *Guidebook on Molecular Modeling in Drug Design* (1996) Academic Press; and W. B. Smith, *Introduction to Theoretical Organic Chemistry and Molecular Modeling* (1996). U.S. Patents which provide detailed information on molecular modeling include, for example: U.S. Pat. Nos. 6,093,573; 6,080,576; 6,075,014; 6,075,123; 6,071,700; 5,994,503; 5,884,230; 5,612,894; 5,583,973; 5,030,103; 4,906,122; and 4,812,128.

Three-dimensional modeling can include, but is not limited to, making three-dimensional representations of structures, drawing pictures of structures, building physical models of structures, and determining the structures of antibiotics, protein synthesis modulators, and/or derivatives or analogs thereof, ribosomes, ribosomal subunits, and complexes thereof. The appropriate co-ordinates can be entered into one or more computer programs for molecular modeling, as known in the art. By way of illustration, a list of computer programs useful for viewing or manipulating three-dimensional structures include: Midas (University of California, San Francisco); MidasPlus (University of California, San Francisco); MOIL (University of Illinois); Yummie (Yale University); Sybyl (Tripos, Inc.); Insight/Discover (Biosym Technologies); MacroModel (Columbia University); Quanta (Molecular Simulations, Inc.); Cerius (Molecular Simulations, Inc.); Alchemy (Tripos, Inc.); LabVision (Tripos, Inc.); Rasmol (Glaxo Research and Development); Ribbon (University of Alabama); NAOMI (Oxford University); Explorer Eyechem (Silicon Graphics, Inc.); Univision (Cray Research); Molscript (Uppsala University); Chem-3D (Cambridge Scientific); Chain (Baylor College of Medicine); O (Uppsala University); GRASP (Columbia University); X-Plor (Molecular Simulations, Inc.; Yale University); Spartan (Wavefunction, Inc.); Catalyst (Molecular Simulations, Inc.); Molcadd (Tripos, Inc.); VMD (University of Illinois/Beckman Institute); Sculpt (Interactive Simulations, Inc.); Procheck (Brookhaven National Library); DGEOM (QCPE); RE_VIEW (Brunell University); Modeller (Birbeck College, University of London); Xmol (Minnesota Supercomputing Center); Protein Expert (Cambridge Scientific); HyperChem (Hypercube); MD Display (University of Washington); PKB (National Center for Biotechnology Information, NIH); ChemX (Chemical Design, Ltd.); Cameleon (Oxford Molecular, Inc.); and Iditis (Oxford Molecular, Inc.).

One approach to RDD is to search for known molecular structures that might bind to a site of interest. Using molecular modeling, RDD programs can look at a range of different molecular structures of molecules that can fit into a site of interest, and by moving them on the computer screen or via computation it can be decided which structures actually fit the E-site well (William Bains (1998) *Biotechnology from A to Z*, second edition, Oxford University Press, p. 259).

An alternative but related approach starts with the known structure of a complex with a small molecule ligand and models modifications of that small molecule in an effort to make additional favorable interactions with a ribosome or ribosomal subunit.

The present invention permits the use of molecular and computer modeling techniques to design and select novel molecules, such as antibiotics or other therapeutic agents, that interact with ribosomes and ribosomal subunits. Such antibiotics and other types of therapeutic agents include, but are not limited to, antifungals, antivirals, antibacterials, insecticides, herbicides, miticides, rodentcides, etc.

In order to facilitate molecular modeling and/or RDD the skilled artisan can use some or all of the atomic co-ordinates recorded on Disk 1, under file names microhelix.pdb, microhelixa.pdb, and 1JJ2.pdb. By using the foregoing atomic co-ordinates, the skilled artisan can design new modulators of protein synthesis that can be tailored to be effective against ribosomes from one or more species but which have little or no effect on ribosomes of other species. The atomic co-ordinates provided herein also permit probing the three-dimensional structure of a ribosome or ribosome subunit or a portion thereof with molecules composed of a variety of different chemical features to determine optimal sites for interaction between candidate molecules and the ribosome or ribosomal subunit. Small molecules that bind those sites can then be designed, synthesized and tested for inhibitory activity (Travis (1993) Science 262: 1374). These molecules can represent lead compounds from which further drug-like compounds can be synthesized.

b. Identification of Target Sites

The atomic co-ordinates of the invention permit the skilled artisan to identify target locations in a ribosome or large ribosomal subunit that can serve as a starting point in rational drug design. As a threshold matter, the atomic co-ordinates permit the skilled artisan to identify specific regions within a ribosome or ribosomal subunit that are involved with protein synthesis in, and/or protein secretion out of, the ribosome. Furthermore, the atomic co-ordinates permit a skilled artisan to further identify portions of these regions that are conserved or are not conserved between different organisms. For example, by identifying portions of these regions that are conserved among certain pathogens, for example, certain prokaryotes, but are not conserved in a host organism, for example, a eukaryote, more preferably a mammal, the skilled artisan can design molecules that selectively inhibit or disrupt protein synthesis activity of the pathogen's but not the host's ribosomes. Furthermore, by analyzing regions that are either conserved or non-conserved between certain pathogens, it can be possible to design broad or narrow spectrum protein synthesis inhibitors, e.g., antibiotics, as a particular necessity arises.

Figure 5:
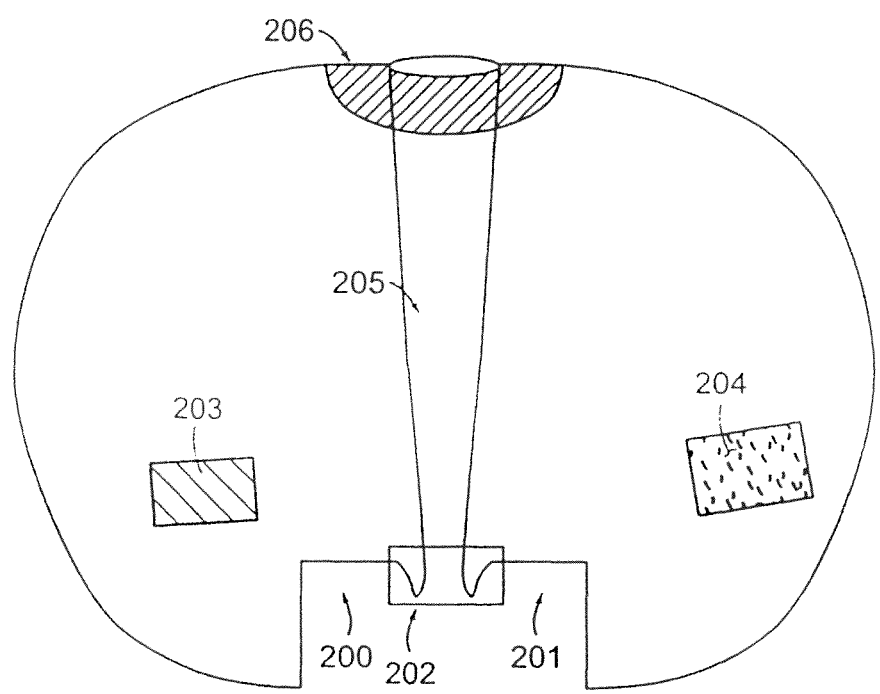
FIG. 5 is a schematic representation of certain potential drug target sites in a large ribosomal subunit.

FIG. 5 is a schematic representation of a large ribosomal subunit that identifies a variety of exemplary target sites that appear to participate in protein synthesis within the ribosome and/or the export or translocation of the newly synthesized protein out of the ribosome. Inspection of the atomic co-ordinates of the *H. marismortui* 50S ribosomal subunit has identified a variety of target regions that can serve as a basis for the rational drug design of new or modified protein synthesis inhibitors. The target regions include a P-site (200 in FIG. 5), an A-site (201 in FIG. 5), a peptidyl transferase-site (202 in FIG. 5) which includes a portion of the P-site and the A-site, an E-site (203 in FIG. 5), a factor binding domain (204 in FIG. 5) including, for example, the EF-Tu binding domain and the EF-G binding domain, the polypeptide exit tunnel (205 in FIG. 5) including cavities defined by the wall of the exit tunnel, and the signal recognition particle binding domain (206 of FIG. 5). Residues that together define at least a portion of the A-site, the P-site, the peptidyl transferase E-site, and the polypeptide tunnel are described, for example, in US Patent Publication Nos. US 2002/0086308 and US 2003/0153002.

Table 1 identifies the residues in the *H. marismortui* 50S ribosomal subunit that together define at least a portion of the RNA microhelix binding site (5.8 Å shell). In addition, Table 1 also identifies the corresponding residues that define at least a portion of the same binding site in *E. coli*, *Rattus*, human, and human mitochondria large subunit. Table 2 identifies the residues in the *H. marismortui* 50S ribosomal subunit that together define a broader portion of the RNA microhelix binding site (5.8 Å-12.6 Å shell). The non-conserved residues were identified by comparison of sequences from the structure of *H. marismortui* 23S rRNA or ribosomal protein that form the above-mentioned sites with the corresponding sequences of aligned genomic DNA encoding either the homologous 23S rRNA or ribosomal protein from the other organisms. Sequence alignments can be determined with the program MegAlign (DNA STAR, Madison, Wis., USA) using default parameters.

TABLE 1

Residues that Define the Microhelix Binding Pocket (5.8 Å shell)

| *H. marismortui* Residue | Corresponding Residue in *E. coli* | Corresponding Residue in *Rattus* | Corresponding Residue in Human | Corresponding Residue in Human Mitochondria |
|---|---|---|---|---|
| 23S rRNA | | | | |
| C220 | C249 | C92 | C92 | C79 |
| C1906 | G1850 | G3444 | G3683 | — |
| U1907 | U1851 | U3445 | U3684 | — |
| G1908 | U1852 | C3446 | C3685 | — |
| A1909 | A1853 | A3447 | A3686 | — |
| G1926 | A1885 | A3462 | A3701 | — |
| G1932 | G1891 | G3468 | G3707 | — |
| G1933 | C1892 | C3469 | C3708 | — |
| A1934 | C1893 | G3470 | G3709 | — |
| C1935 | C1894 | C3471 | C3710 | — |
| C2268 | G2235 | G3901 | G4140 | U1129 |
| C2269 | U2236 | U3902 | U4141 | U1130 |
| A2429 | A2392 | A4060 | A4299 | A1227 |
| A2430 | U2393 | U4061 | U4300 | U1228 |
| C2431 | C2394 | C4062 | C4301 | C1229 |
| C2432 | C2395 | C4063 | C4302 | C1230 |
| G2459 | G2421 | G4091 | G4330 | G1239 |
| A2460 | C2422 | G4092 | G4331 | A1240 |
| A2468 | A2433 | A4100 | A4339 | C1250 |
| Protein L44E | | | | |
| R29 | — | K30 | K30 | — |
| I36 | — | G37 | G37 | — |
| R40 | — | Y41 | Y41 | — |
| K51 | — | T52 | T52 | — |
| F52 | — | K53 | K53 | — |
| S53 | — | P54 | P54 | — |
| K54 | — | I55 | I55 | — |
| V55 | — | F56 | F56 | — |
| P56 | — | R57 | R57 | — |
| G57 | — | K58 | K58 | — |
| G58 | — | K59 | K59 | — |

Residues were determined as a 5.8 angstrom distance measurement (atom center to atom center) between the atoms of the deacylated tRNA microhelix and the 50S ribosome using the program SPOCK[a]. Conserved residues were determined by comparison between the proposed structures of *H. marismortui*[b], *E. coli*[c], and *Rattus norvegicus*[d], Human[e], and Human Mitochondria[f]. A dash (—) means a homologous residue is not present.
[a]Christopher, Jon A. (1998) SPOCK: The Structural Properties Observation and Calculation Kit (Program Manual), The Center for Macromolecular Design, Texas A&M University, College Station, TX.
[b]Genbank entries AF034620 (RNA), P32411 (protein L44E). The sequence of 1JJ2.pdb and Genbank entry AF034620 are identical but the numbering is offset by one residue for the Genbank entry (i.e., lower by one).
[c]Genbank entry NC_000913 (RNA).
[d]Genbank entries X01069 (RNA) and R6RT36 (protein L44E).
[e]Genbank entries M11167 (RNA) and P09896 (protein L44E).
[f]Genbank entry V00710 (RNA).

TABLE 2

Residues that Further Define the Microhelix Binding Pocket (5.8 Å-12.6 Å shell)

| *H. marismortui* Residue | Corresponding Residue in *E. coli* | Corresponding Residue in *Rattus* | Corresponding Residue in Human | Corresponding Residue in Human Mitochondria |
|---|---|---|---|---|
| 23S rRNA | | | | |
| A169 | A199 | A42 | A42 | A57 |
| U170 | U200 | U43 | U43 | U58 |
| C218 | G247 | G90 | G90 | G77 |
| G219 | G248 | G91 | G91 | G78 |

TABLE 2-continued

Residues that Further Define the Microhelix
Binding Pocket (5.8 Å-12.6 Å shell)

| H. marismortui Residue | Corresponding Residue in E. coli | Corresponding Residue in Rattus | Corresponding Residue in Human | Corresponding Residue in Human Mitochondria |
|---|---|---|---|---|
| G221 | G250 | G93 | G93 | G80 |
| G1896 | G1840 | G3433 | G3672 | G881 |
| U1897 | U1841 | U3434 | U3673 | U882 |
| G1898 | G1842 | G3435 | G3674 | G883 |
| A1904 | A1848 | A3442 | A3681 | — |
| U1905 | G1849 | U3443 | U3682 | — |
| A1910 | A1854 | A3448 | A3687 | — |
| A1924 | U1883 | U3460 | U3699 | — |
| G1925 | G1884 | C3461 | C3700 | — |
| A1927 | A1886 | A3463 | A3702 | — |
| C1928 | C1887 | U3464 | U3703 | — |
| G1929 | G1888 | G3465 | G3704 | — |
| A1930 | A1889 | G3466 | A3705 | — |
| A1931 | A1890 | A3467 | A3706 | — |
| C1936 | C1895 | G3472 | G3711 | — |
| A2118 | A2077 | A3653 | A3892 | A1070 |
| C2119 | C2078 | C3654 | C3893 | A1071 |
| U2120 | U2079 | U3655 | U3894 | U1072 |
| G2121 | A2080 | C3656 | C3895 | U1073 |
| A2266 | U2233 | A3899 | A4138 | C1127 |
| G2267 | G2234 | G3900 | G4139 | A1128 |
| G2270 | G2237 | G3903 | G4142 | A1131 |
| C2317 | C2283 | U3950 | U4189 | C1177 |
| A2398 | G2361 | C4029 | C4268 | — |
| G2399 | C2362 | G4030 | G4269 | — |
| C2427 | U2390 | C4058 | C4297 | U1225 |
| G2428 | G2391 | C4059 | G4298 | G1226 |
| A2433 | G2396 | U4064 | U4303 | A1231 |
| A2434 | G2397 | U4065 | U4304 | U1232 |
| G2452 | G2414 | A4084 | A4323 | — |
| A2456 | A2418 | G4088 | G4327 | C1236 |
| U2457 | C2419 | G4089 | G4328 | U1237 |
| U2458 | G2420 | A4090 | A4329 | U1238 |
| U2461 | C2424 | U4093 | U4332 | C1242 |
| G2462 | G2425 | G4094 | G4333 | A1243 |
| G2466 | G2429 | G4098 | G4337 | G1247 |
| A2467 | A2430 | A4099 | A4338 | A1248 |
| A2469 | A2434 | A4101 | A4340 | A1251 |
| Protein L44E | | | | |
| V25 | — | Y26 | Y26 | — |
| R26 | — | K27 | K27 | — |
| S27 | — | K28 | K28 | — |
| G28 | — | G29 | G29 | — |
| Q30 | — | D31 | D31 | — |
| T31 | — | S32 | S32 | — |
| G32 | — | L33 | L33 | — |
| M33 | — | Y34 | Y34 | — |
| K34 | — | A35 | A35 | — |
| W35 | — | Q36 | Q36 | — |
| D37 | — | K38 | K38 | — |
| R38 | — | R39 | R39 | — |
| Q39 | — | R40 | R40 | — |
| E41 | — | D42 | D42 | — |
| R42 | — | R43 | R43 | — |
| N43 | — | K44 | K44 | — |
| S44 | — | Q45 | Q45 | — |
| N48 | — | G49 | G49 | — |
| D49 | — | G50 | G50 | — |
| G50 | — | Q51 | Q51 | — |
| D59 | — | A60 | A60 | — |
| K60 | — | K61 | K61 | — |
| P61 | — | T62 | T62 | — |
| T62 | — | T63 | T63 | — |
| K63 | — | K64 | K64 | — |
| K64 | — | K65 | K65 | — |
| T65 | — | I66 | I66 | — |
| D66 | — | V67 | V67 | — |
| R84 | — | R87 | R87 | — |
| Protein L15 | | | | |
| L46 | L61 | F53 | F53 | I78 |
| G47 | P62 | G54 | G54 | P79 |
| K48 | K63 | K55 | K55 | K80 |

Residues were determined as a 5.8-12.6 angstrom distance measurement (atom center to atom center) between the atoms of the deacylated tRNA microhelix and the 50S ribosome using the program SPOCK[a]. Conserved residues were determined by comparison between the proposed structures of H. marismortui[b], E. coli[c], and Rattus norvegicus[d], Human[e], and Human Mitochondria[f]. A dash (—) means a homologous residue is not present.
[a]Christopher, Jon A. (1998) SPOCK: The Structural Properties Observation and Calculation Kit (Program Manual), The Center for Macromolecular Design, Texas A&M University, College Station, TX.
[b]Genbank entries AF034620 (RNA), P32411 and R6HS15 (proteins L44E and L15, respectively). The sequence of 1JJ2.pdb and Genbank entry AF034620 are identical but the numbering is offset by one residue for the Genbank entry (i.e., lower by one).
[c]Genbank entries NC_000913 (RNA) and NP_417760 (protein L15).
[d]Genbank entries X01069 (RNA), R6RT36 and R5RTLA (proteins L44E and L15, respectively).
[e]Genbank entries M11167 (RNA), P09896 and NP_000981 (proteins L44E and L15, respectively).
[f]Genbank entries V00710 (RNA) and NP_054894 (protein L15).

The skilled artisan, when in possession of the foregoing or other exemplary target sites, can use the process of rational drug design to identify molecules that potentially bind to one or more of the target sites and/or inhibit ribosomal activity. Furthermore, by taking into account which of the residues that define the target site are conserved between pathogens but not conserved between host species, the skilled artisan can design new species-specific protein synthesis inhibitors. It is apparent that the skilled artisan can take advantage of the regions that are not conserved between E. coli and rat or human to provide target regions for rational drug design.

c. Identification of Candidate Molecules

It is contemplated that candidate molecules that modulate protein biosynthesis can be designed entirely de novo or can be based upon one or more pre-existing molecules. Either of these approaches can be facilitated by computationally screening databases and libraries of small molecules for chemical entities, agents, ligands, or compounds that can bind in whole, or in part, to ribosomes and ribosomal subunits, or alternatively to large ribosomal subunits, and yet alternatively to 50S ribosomal subunits. In this screening, the quality of fit of such entities or compounds to the binding site or sites can be judged either by shape complementarity or by estimated interaction energy (Meng et al. (1992) J. Comp. Chem. 13: 505-524).

The design of molecules that bind to and/or inhibit the functional activity of ribosomes or ribosomal subunits generally involves consideration of two factors. First, the molecule must be capable of physically and structurally associating with the large ribosomal subunit. Non-covalent molecular interactions important in the association of ribosomes and ribosomal subunits with the molecule, include hydrogen bonding, van der Waals and hydrophobic interactions. Second, the molecule must be able to assume a conformation that allows it to associate with the ribosomes or ribosomal subunits, and more preferably with the large ribosomal subunits.

The candidate molecule and analogs or derivatives of the candidate molecule (also referred to as a modified candidate molecule), preferably bind specifically or have binding specificity to the large ribosomal unit, as does a RNA microhelix. For example, the candidate molecule and the modified candidate molecule preferably bind to, for example, no greater than 5, optionally less than 5, optionally less than 4, optionally less than 3, optionally less than 2 ribofunctional loci in a large ribosomal subunit. Preferably, the candidate molecule or modified candidate molecule binds to a single ribofunctional locus, for example, at least a portion of the corresponding RNA microhelix binding site of the large ribosomal subunit, to modulate ribosome function.

Preferably, the candidate molecule or modified candidate molecule binds to, for example, at least a portion of the microhelix binding site of the large ribosomal subunit, to modulate ribosome function. As discussed hereinabove, the microhelix binding site comprises a plurality of residues listed in Table 1. Table 1 lists, for example, 30 residues that contribute to the microhelix binding pocket. The candidate molecule and the modified candidate molecule when they bind specifically to the microhelix binding site contact 4 to 30, 5 to 25, 6 to 30, 7 to 15, and 8 to 10 of the residues listed in Table 1. Preferably, when the candidate molecule and the modified candidate molecule binds specifically to the microhelix binding site, the molecule contacts at least 6, optionally at least 8, and optionally at least 10, of the residues listed in Table 1.

Although certain portions of the candidate molecule do not directly participate in this association with a ribosome or ribosomal subunits, those portions can still influence the overall conformation of the molecule. This, in turn, can have an effect on binding affinities, therapeutic efficacy, drug-like qualities, and potency. Such conformational requirements include the overall three-dimensional structure and orientation of the chemical entity or molecule in relation to all or a portion of the active-site or other region of the ribosomes or ribosomal subunits, or the spacing between functional groups of a molecule comprising several chemical entities that directly interact with the ribosomes or ribosomal subunits, alternatively with the large ribosomal subunits, and yet alternatively with the 50S ribosomal subunit.

The potential, predicted, inhibitory or binding effect of a molecule on ribosomes and ribosomal subunits can be analyzed prior to its actual synthesis and testing by the use of computer modeling techniques. If the theoretical structure of the given molecule suggests insufficient interaction and association between it and ribosomes or ribosomal subunits, synthesis and testing of the molecule is obviated. However, if computer modeling indicates a strong interaction, the molecule can then be synthesized and tested for its ability to interact with the ribosomes or ribosomal subunits and inhibit protein synthesis. In this manner, synthesis of inoperative molecules can be avoided. The synthesis and characterization of such molecules permits the development of structure-activity relationships, which can then be used in the iterative refinement of the molecules of interest.

d. De Novo Design

One skilled in the art can use one of several methods to identify chemical moieties or entities, compounds, or other agents for their ability to associate with a preselected target site within a ribosomes or ribosomal subunit. This process can begin by visual inspection or computer assisted modeling of, for example, the target site on the computer screen based on the atomic co-ordinates of microhelix and/or protein synthesis modulator either alone or in association with the 50S ribosomal subunit. In one embodiment, molecule design uses computer modeling programs which calculate how different molecules interact with the various sites of the ribosome, ribosomal subunit, or a fragment thereof. Selected chemical moieties or entities, compounds, or agents can then be positioned in a variety of orientations, or docked, within at least a portion of the target site of a ribosome or ribosomal subunit, more preferably of a large ribosomal subunit, and even more preferably of a 50S ribosomal subunit. Databases of chemical structures are available from, for example, Cambridge Crystallographic Data Center (Cambridge, U.K.) and Chemical Abstracts Service (Columbus, Ohio). Docking can be accomplished using software such as Cerius, Quanta or Sybyl, followed by energy minimization and molecular dynamics with standard molecular mechanics forcefields, such as OPLS-AA, CHARMM or AMBER.

Specialized computer programs can also assist in the process of selecting chemical entities. These include, but are not limited to:

(1) GRID (Goodford, P. J., "A Computational Procedure for Determining Energetically Favorable Binding Sites on Biologically Important Macromolecules" (1985) *J. Med. Chem.* 28, 849-857). Software such as GRID, a program that determines probable interaction sites between probes with various functional group characteristics and the macromolecular surface, can be used to analyze the surface sites to determine structures of similar inhibiting proteins or molecules. The GRID calculations, with suitable inhibiting groups on molecules (e.g., protonated primary amines) as the probe, are used to identify potential hotspots around accessible positions at suitable energy contour levels. GRID is available from Oxford University, Oxford, UK.

(2) MCSS (Miranker, A. and M. Karplus (1991) "Functionality Maps of Binding Sites: A Multiple Copy Simultaneous Search Method." *Proteins: Structure, Function and Genetics* 11: 29-34). MCSS is available from Molecular Simulations, Burlington, Mass.

(3) AUTODOCK (Goodsell, D. S, and A. J. Olsen (1990) "Automated Docking of Substrates to Proteins by Simulated Annealing" *Proteins: Structure, Function, and Genetics* 8: 195-202). AUTODOCK is available from Scripps Research Institute, La Jolla, Calif.

(4) DOCK (Kuntz, I. D. et al. (1982) "A Geometric Approach to Macromolecule-Ligand Interactions" *J. Mol. Biol.* 161: 269-288). The program DOCK can be used to analyze an active site or ligand binding site and suggest ligands with complementary steric properties. DOCK is available from University of California, San Francisco, Calif.

(5) ALADDIN (Van Drie et al. (1989) "ALADDIN: An Integrated Tool of Computer Assisted Molecular Design and Pharmacophore Recognition From Geometric, Steric and Substructure Searching of Three-Dimensional Structures" *J. Comp-Aided Mol. Des.* 3: 225).

(6) CLIX (Davie and Lawrence (1992) "CLIX: A Search Algorithm for Funding Novel Ligands Capable of Binding Proteins of Known Three-Dimensional Structure" *Proteins* 12: 31-41).

(7) GROUPBUILD (Rotstein and Murcko (1993) "GroupBuild: A Fragment-Based Method for De Novo Drug Design" *J. Med. Chem.* 36: 1700).

(8) GROW (Moon and Howe (1991) "Computer Design of Bioactive Molecules: A Method for Receptor-Based De Novo Ligand Design" *Proteins* 11: 314).

Once suitable chemical moieties or entities, compounds, or agents have been selected, they can be assembled into a single molecule. Assembly can proceed by visual inspection and/or computer modeling and computational analysis of the spatial relationship of the chemical moieties or entities, compounds or agents with respect to one another in three-dimensional space. This could then be followed by model building using software such as Quanta or Sybyl.

Useful programs to aid one of skill in the art in connecting the individual chemical entities, compounds, or agents include but are not limited to:

(1) CAVEAT (Bartlett, P. A. et al. (1989) "CAVEAT: A Program to Facilitate the Structure-Derived Design of Biologically Active Molecules". In molecular Recognition in Chemical and Biological Problems", Special Pub., *Royal Chem. Soc.* 78: 82-196) and (Bacon et al. (1992) *J. Mol. Biol.* 225: 849-858). CAVEAT uses databases of cyclic compounds which can act as "spacers" to connect any number of chemical fragments already positioned in the active site. This allows one skilled in the art to quickly generate hundreds of possible ways to connect the fragments already known or suspected to be necessary for tight binding. CAVEAT is available from the University of California, Berkeley, Calif.

(2) 3D Database systems such as MACCS-3D (MDL Information Systems, San Leandro, (CA). This area is reviewed in Martin, Y. C., (1992) "3D Database Searching in Drug Design", *J. Med. Chem.* 35: 2145-2154.

(3) HOOK (available from Molecular Simulations, Burlington, Mass.).

Instead of proceeding to build a molecule of interest in a step-wise fashion one chemical entity at a time as described above, the molecule of interest can be designed as a whole using either an empty active site or optionally including some portion or portions of a preselected molecule. Software that implements these methods include:

(1) LUDI (Bohm, H.-J. (1992) "The Computer Program LUDI: A New Method for the De Novo Design of Enzyme Inhibitors" *J. Comp. Aid. Molec. Design* 6: 61-78). The program LUDI can determine a list of interaction sites into which to place both hydrogen bonding and hydrophobic fragments. LUDI then uses a library of approximately 600 linkers to connect up to four different interaction sites into fragments. Then smaller "bridging" groups such as —$CH_2$— and —COO— are used to connect these fragments. For example, for the enzyme DHFR, the placements of key functional groups in the well-known inhibitor methotrexate were reproduced by LUDI. See also, Rotstein and Murcko, (1992) *J. Med. Chem.* 36:1700-1710. LUDI is available from Biosym Technologies, San Diego, Calif.

(2) LEGEND (Nishibata, Y. and A. Itai (1991) *Tetrahedron* 47, 8985) (available from Molecular Simulations, Burlington, Mass.).

(3) LeapFrog (available from Tripos Associates, St. Louis, Mo.).

(4) Aladdin (available from Daylight Chemical Information Systems, Irvine, Calif.)

Other molecular modeling techniques can also be employed in accordance with this invention. See, e.g., Cohen, N. C. et al. (1990) "Molecular Modeling Software and Methods for Medicinal Chemistry, *J. Med. Chem.* 33: 883-894. See also, Navia, M. A. and M. A. Murcko (1992) "The Use of Structural Information in Drug Design", *Current Opinions in Structural Biology* 2: 202-210; and Jorgensen (1998) "BOSS— Biochemical and Organic Simulation System" in the *Encyclopedia of Computational Chemistry* (P. V. R. Schleyer, ed.) Wiley & Sonstra., Athens, U.S.A. 5: 3281-3285).

It is contemplated that during modeling, it can be possible to introduce into the molecule of interest, chemical moieties that can be beneficial for a molecule that is to be administered as a pharmaceutical. For example, it can be possible to introduce into or omit from the molecule of interest, chemical moieties that can not directly affect binding of the molecule to the target area but which contribute, for example, to the overall solubility of the molecule in a pharmaceutically acceptable carrier, the bioavailability of the molecule and/or the toxicity of the molecule. Considerations and methods for optimizing the pharmacology of the molecules of interest can be found, for example, in "Goodman and Gilman's The Pharmacological Basis of Therapeutics" Eighth Edition (Goodman, Gilman, Rall, Nies, & Taylor (eds.)) Pergaman Press (1985); Jorgensen & Duffy (2000) *Bioorg. Med. Chem. Lett.* 10: 1155-1158.

Furthermore, the computer program "Qik Prop" can be used to provide rapid predictions for physically significant descriptions and pharmaceutically-relevant properties of an organic molecule of interest. A 'Rule of Five' probability scheme can be used to estimate oral absorption of the newly synthesized compounds (Lipinski et al. (1997) *Adv. Drug Deliv. Rev.* 23:3).

Programs suitable for pharmacophore selection and design include:

(1) DISCO (Abbot Laboratories, Abbot Park, Ill.).

(2) Catalyst (Bio-CAD Corp., Mountain View, Calif.).

(3) Chem DBS-3D (Chemical Design Ltd., Oxford, U.K.).

Furthermore, the skilled artisan can use the information available on how to design suitable therapeutically active and pharmaceutically useful compounds, and use this information in the design of new protein synthesis modulators. See, for example, Lipinski et al. (1997) *Ad. Drug Deliv. Reviews* 23: 3-25; Van de Waterbeemd et al. (1996) *Quantitative Structure Activity Relationships* 15: 480-490; and Cruciani et al. (2000) *Theochem-J. Mol. Struct.* 503: 17-30.

The entry of the co-ordinates of the ribosome's or ribosomal subunit's proteins and RNAs into the computer programs discussed above facilitates the calculation of most probable structure of the macromolecule, including overall atomic co-ordinates of a ribosome, ribosomal subunit or a fragment thereof. These structures can be combined and refined by additional calculations using such programs to determine the probable or actual three-dimensional structure of the ribosome, ribosomal subunit or a fragment thereof, including potential or actual active or binding sites of ligands.

e. Modification of Existing Molecules

Instead of designing molecules of interest entirely de novo it is contemplated that pre-existing molecules or portions thereof can be used as a starting point for the design of a new candidate. It is contemplated that many of the approaches useful for designing molecules de novo can also be useful for modifying existing molecules.

It is contemplated that knowledge of the spatial relationship between a modulator of protein biosynthesis, for example, an antibiotic, and its respective binding site within a ribosome permits the design of modified modulator that can have better binding properties, for example, higher binding affinity and/or binding specificity, relative to the molecule from which it was derived. Alternatively, knowledge of modulator contact sites within a ribosome permits the synthesis of a new molecule that contains, for example, a portion of a first molecule (for example, an antibiotic or an analog or derivative) that binds to the contact site and another portion that contributes additional functionality.

It is contemplated that a variety of modified molecules (for example, modified protein synthesis modulators) can be designed using the atomic co-ordinates provided herein. For example, it is contemplated that by knowing the spatial relationship of one or more of protein synthesis modulators relative to the large ribosomal subunit it is possible to generate new modulator molecules. The atomic co-ordinates of each protein synthesis modulator relative to the large ribosomal subunit provide information on what portions of the ribosome or ribosomal subunit and the protein synthesis modulator contact one, another. Accordingly; from this information the skilled artisan can not only identify contact locations within the ribosome that can be used for de novo drug design, as discussed above, but also can identify portions of an protein synthesis modulator that can act as a ribosome binding domain.

The atomic co-ordinates provided herein permit the skilled artisan to use the information pertaining to identify a ribosome binding domain and to design other modulators of protein biosynthesis. For example, with an understanding of the ribosome contact region and the surrounding environment, the skilled artisan can provide novel molecules, a portion of which is based upon the antibiotic binding region (binding domain) and another portion of which (effector domain) can be designed as a novel space filling domain that sterically inhibits or disrupts protein biosynthesis within the ribosome or secretion through the polypeptide exit tunnel. For example, the skilled artisan can combine a ribosome binding region of the RNA microhelix, which binds to one side of the E-site with, for example, a novel chemical moiety, for example, a moiety not present in antibiotics identified to date, that is bulky enough to block the E-site more effectively. However, it is contemplated that the skilled artisan can take advantage of one or more of the many of the antibiotic contact regions disclosed herein to design entirely new binding and effector domains.

The resulting candidate molecules (protein synthesis modulators, for example, protein synthesis inhibitors), can have a molecular weight no greater than about 1,500, optionally no greater than about 1,000, optionally no greater than 750 and, optionally no greater than about 500. The protein synthesis inhibitors can have a molecular weight in the range from about 250 to about 1500, and optionally in the range from about 500 to about 1200. In addition, the protein synthesis inhibitors have a minimal inhibitor concentration optionally no greater than 50 µM, optionally no greater than 10 µM, and optionally no greater than 1 µM to inhibit 50% activity ($IC_{50}$) in a biological assay, for example, an in vitro translation assay, for example, an E. coli translation assay. The protein synthesis inhibitors can have an $IC_{50}$ in the range from about 0.001 µM to about 50 µM, optionally in the range from about 0.01 µM to about 10 µM, and optionally in the range from about 0.1 µM to about 1 µM.

Furthermore, the present invention permits the skilled artisan to design molecules, for example, selective protein synthesis inhibitors that are tailored to be more potent with respect to ribosomes of a target organism, for example, a pathogen such a microbe, and less potent, i.e., less toxic, to ribosomes of a non target organism, for example, host organism such as a human. Also, the invention permits the skilled artisan to use the atomic co-ordinates and structures of the large ribosomal subunit and its complexes with protein synthesis inhibitors to design modifications to starting compounds, such as an antibiotic, that will bind more tightly to a target ribosome (e.g., the 50S ribosomal subunit of bacteria) and less tightly to a non-targeted ribosome (e.g., human 60S ribosomal subunit or a human mitochondrial ribosome).

The structure of a complex between the large ribosomal subunit and the starting compound (e.g., the RNA microhelix) can also be used to guide the modification of that compound to produce new compounds that have other desirable properties for the applicable industrial and other uses (e.g., as pharmaceuticals, herbicides or insecticides), such as chemical stability, solubility or membrane permeability.

The novel agents contemplated by the present invention can be useful as herbicides, pesticides (e.g., insecticides, nematocides, rodenticides, etc.), miticides, or antimicrobial agents (e.g., antifungals, antibacterials, antiprotozoals, etc.) to target specific organisms. For example, the novel agents can target animal and plant parasitic nematodes, prokaryotic organisms (disease causing microbes), and eukaryotic multicellular pests. Specific examples of multicellular pests include, but are not limited to, insects, fungi, bacteria, nematodes, mites and ticks, protozoan pathogens, animal-parasitic liver flukes, and the like.

Once a candidate molecule has been designed or selected by the above methods, the affinity with which that molecule can bind to the ribosome or ribosomal subunit can be tested and optimized by computational evaluation and/or by testing biological activity after synthesizing the compound. Candidate molecules can interact with the ribosomes or ribosomal subunits in more than one conformation, each of which has a similar overall binding energy. In those cases, the deformation energy of binding can be considered to be the difference between the energy of the free molecule and the average energy of the conformations observed when the molecule binds to the ribosomes or ribosomal subunits, more preferably to the large ribosomal subunits, and even more preferably to the 50S ribosomal subunits. A molecule designed or selected as binding to a ribosome or ribosomal subunit can be further computationally optimized so that in its bound state it preferably lacks repulsive electrostatic interaction with the target region. Such non-complementary (e.g., electrostatic) interactions include repulsive charge-charge, dipole-dipole and charge-dipole interactions.

Specific computer programs that can evaluate a compound deformation energy and electrostatic interaction are available in the art. Examples of suitable programs include: Gaussian 92, revision C (M. J. Frisch, Gaussian, Inc., Pittsburgh, Pa.); AMBER, version 4.0 (P. A. Kollman, University of California at San Francisco, Calif.); QUANTA/CHARMM (Molecular Simulations, Inc., Burlington, Mass.); OPLS-AA ("OPLS Force Fields." W. L. Jorgensen. Encyclopedia of Computational Chemistry, Schleyer, Ed.; Wiley: New York, 1998; Vol. 3, pp 1986-1989) and Insight II/Discover (Biosysm Technologies Inc., San Diego, Calif.). These programs can be implemented, for instance, using a Silicon Graphics workstation, IRIS 4D/35 or IBM RISC/6000 workstation model 550. Other hardware systems and software packages are known to those skilled in the art.

Once a molecule of interest has been selected or designed, as described above, substitutions can then be made in some of its atoms or side groups in order to improve or modify its binding properties. Generally, initial substitutions are conservative, i.e., the replacement group will approximate the same size, shape, hydrophobicity and charge as the original group. It should, of course, be understood that components known in the art to alter conformation should be avoided. Such substituted chemical compounds can then be analyzed for efficiency of fit to the ribosome or ribosomal subunit by the same computer methods described in detail, above. In addition, once synthesized, the structure of the candidate molecule when disposed within the 50S ribosomal subunit can be determined by X-ray diffraction studies. Based on the resulting structures, the skilled artisan can use this information to modify and optimize the candidate molecule using the procedures described herein.

3. Synthesis of Candidate Molecules

A candidate molecule of the present invention can be, but is not limited to, at least one selected from a lipid, nucleic acid, peptide, small organic or inorganic molecule, chemical compound, element, saccharide, isotope, carbohydrate, imaging agent, lipoprotein, glycoprotein, enzyme, analytical probe, and an antibody or fragment thereof, any combination of any of the foregoing, and any chemical modification or variant of any of the foregoing. In addition, a lead molecule can optionally comprise a detectable label. Such labels include, but are not limited to, enzymatic systems, radioisotopes and spectroscopic labels, for example, radioactive compounds, fluorescent compounds, spin labels, chemiluminescent compounds and bioluminescent compounds.

Methods useful for synthesizing lead molecules such as lipids, nucleic acids, peptides, small organic or inorganic molecules, chemical compounds, elements, saccharides, isotopes, carbohydrates, imaging agents, lipoproteins, glycoproteins, enzymes, analytical probes, antibodies, and antibody fragments are well known in the art. Such methods include the traditional approach of synthesizing one such candidate molecule at a time, as well as the simultaneous synthesis of multiple candidate molecules by combinational chemistries. Methods for the simultaneous synthesis of multiple candidate molecules are particularly useful in preparing combinatorial libraries, which can be used in screening techniques known in the art.

4. Characterization of Candidate Molecules

Candidate molecules designed, selected and/or optimized by methods described above, once produced, can be characterized using a variety of assays known to those skilled in the art to determine whether the candidate molecules have biological activity. For example, the candidate molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen candidate molecules for activity, for example, as anti-cancer, anti-bacterial, anti-fungal, anti-parasitic or anti-viral agents. Also, it can be possible to assay how the candidate molecules interact with a ribosome or ribosomal subunit and/or are effective as modulators (for example, inhibitors) of protein synthesis using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

(1) Surface Binding Studies.

A variety of binding assays can be useful in screening new molecules for their binding activity. One approach includes surface plasmon resonance (SPR) which can be used to evaluate the binding properties molecules of interest with respect to a ribosome, ribosomal subunit or a fragment thereof.

SPR methodologies measure the interaction between two or more macromolecules in real-time through the generation of a quantum-mechanical surface plasmon. One device, (BIAcore Biosensor® from Pharmacia Biosensor, Piscatawy, N.J.) provides a focused beam of polychromatic light to the interface between a gold film (provided as a disposable biosensor "chip") and a buffer compartment that can be regulated by the user. A 100 nm thick "hydrogel" composed of carboxylated dextran which provides a matrix for the covalent immobilization of analytes of interest is attached to the gold film. When the focused light interacts with the free electron cloud of the gold film, plasmon resonance is enhanced. The resulting reflected light is spectrally depleted in wavelengths that optimally evolved the resonance. By separating the reflected polychromatic light into its component wavelengths (by means of a prism), and determining the frequencies which are depleted, the BIAcore establishes an optical interface which accurately reports the behavior of the generated surface plasmon resonance. When designed as above, the plasmon resonance (and thus the depletion spectrum) is sensitive to mass in the evanescent field (which corresponds roughly to the thickness of the hydrogel). If one component of an interacting pair is immobilized to the hydrogel, and the interacting partner is provided through the buffer compartment, the interaction between the two components can be measured in real time based on the accumulation of mass in the evanescent field and its corresponding effects of the plasmon resonance as measured by the depletion spectrum. This system permits rapid and sensitive real-time measurement of the molecular interactions without the need to label either component.

(2) Fluorescence Polarization.

Fluorescence polarization (FP) is a measurement technique that can readily be applied to protein-protein, protein-ligand, or RNA-ligand interactions in order to derive $IC_{50}$s and Kds of the association reaction between two molecules. In this technique one of the molecules of interest is conjugated with a fluorophore, usually the smaller molecule in the system (in this case, the molecules of interest). The sample mixture, containing the molecule-probe conjugate and the ribosome, ribosomal subunit or fragment thereof, is excited with vertically polarized light. Light is absorbed by the probe fluorophores, and re-emitted a short time later. The degree of polarization of the emitted light is measured. Polarization of the emitted light is dependent on several factors, but most importantly on viscosity of the solution and on the apparent molecular weight of the fluorophore. With proper controls, changes in the degree of polarization of the emitted light depends only on changes in the apparent molecular weight of the fluorophore, which in-turn depends on whether the probe-ligand conjugate is free in solution, or is bound to a receptor. Binding assays based on FP have a number of important advantages, including the measurement of $IC_{50}$s and Kds under true homogenous equilibrium conditions, speed of analysis and amenity to automation, and ability to screen in cloudy suspensions and colored solutions.

(3) Cellular and Subcellular Assays.

It is contemplated that, in addition to characterization by the foregoing biochemical assays, the molecules of interest can also be characterized as a modulator (for example, an inhibitor of protein synthesis) of the functional activity of the ribosome or ribosomal subunit.

Furthermore, more specific protein synthesis inhibition assays can be performed by administering the molecule to a whole organism, tissue, organ, organelle, cell, a cellular or subcellular extract, or a purified ribosome preparation and observing its pharmacological and inhibitory properties by determining, for example, its inhibition constant ($IC_{50}$) for inhibiting protein synthesis. Incorporation of $^3$H leucine or $^{35}$S methionine, or similar experiments can be performed to investigate protein synthesis activity. A change in the amount or the rate of protein synthesis in the cell in the presence of a molecule of interest indicates that the molecule is a modulator of protein synthesis. A decrease in the rate or the amount of protein synthesis indicates that the molecule is a inhibitor of protein synthesis.

Furthermore, the compounds can be assayed for anti-proliferative or anti-infective properties on a cellular level. For example, where the target organism is a micro-organism, the activity of molecules of interest can be assayed by growing the micro-organisms of interest in media either containing or lacking the molecule. Growth inhibition can be indicative that the molecule can be acting as a protein synthesis inhibitor. More specifically, the activity of the molecules of interest against bacterial pathogens can be demonstrated by the ability of the compound to inhibit growth of defined strains of human pathogens. For this purpose, a panel of bacterial strains can be assembled to include a variety of target pathogenic species, some containing resistance mechanisms that have been characterized. Use of such a panel of organisms permits the determination of structure-activity relationships not only in regards to potency and spectrum, but also with a view to obviating resistance mechanisms. The assays can be performed in microtiter trays according to conventional methodologies as published by The National Committee for Clinical Laboratory Standards (NCCLS) guidelines (NCCLS. M7-A5-Methods for Dilution Antimicrobial Susceptibility Tests for Bacteria That Grow Aerobically; Approved Standard-Fifth Edition, NCCLS Document M100-S12/M7 (ISBN 1-56238-394-9).

5. Drug Formulation and Administration

The active molecules, once identified, can be useful in the prevention or treatment of a variety of human or other animal disorders, including for example, bacterial infection, fungal infections, viral infections, parasitic diseases, and cancer. Typically, once the desired candidate molecule or modified candidate molecule has been identified, it may then be produced in commercially reasonable amounts. These compounds, when produced on an analytical scale are produced on the gram scale, whereas, when produced in a commercially reasonable amount, are produced on the kilogram scale. However, once made on a commercially reasonable scale, the active molecules can be incorporated into any suitable carrier prior to use. The dose of active molecule, mode of administration and use of suitable carrier will depend upon the intended recipient and target organism. The formulations, both for veterinary and for human medical use, typically include such compounds in association with a pharmaceutically acceptable carrier or excipient.

The carrier should be acceptable in the sense of being compatible with the other ingredients of the formulations and not deleterious to the recipient. Pharmaceutically acceptable carriers, in this regard, are intended to include any and all solvents, dispersion media, coatings, anti-bacterial and anti-fungal agents, isotonic and absorption delaying agents, and the like, that are compatible with pharmaceutical administration. The use of such media and agents for pharmaceutically active substances is known in the art. Supplementary active compounds (identified or designed according to the invention and/or known in the art) also can be incorporated into the formulations. The formulations can conveniently be presented in dosage unit form and can be prepared by any of the methods well known in the art of pharmacy/microbiology. In general, some formulations are prepared by bringing the active molecule into association with a liquid carrier or a finely divided solid carrier or both, and then, if necessary, shaping the product into the desired formulation.

A pharmaceutical composition of the invention should be formulated to be compatible with its intended route of administration. Examples of routes of administration include oral or parenteral, for example, intravenous, intradermal, inhalation, transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Useful solutions for oral or parenteral administration can be prepared by any of the methods well known in the pharmaceutical art, described, for example, in *Remington's Pharmaceutical Sciences*, (Gennaro, A., ed.), Mack Pub., (1990). Formulations for parenteral administration can also include glycocholate for buccal administration, methoxysalicylate for rectal administration, or citric acid for vaginal administration. The parenteral preparation can be enclosed in ampuoles, disposable syringes or multiple dose vials made of glass or plastic. Suppositories for rectal administration also can be prepared by mixing the drug with a non-irritating excipient such as cocoa butter, other glycerides, or other compositions which are solid at room temperature and liquid at body temperatures. Formulations also can include, for example, polyalkylene glycols such as polyethylene glycol, oils of vegetable origin, hydrogenated naphthalenes, and the like. Formulations for direct administration can include glycerol and other compositions of high viscosity. Other potentially useful parenteral carriers for these drugs include ethylene-vinyl acetate copolymer particles, osmotic pumps, implantable infusion systems, and liposomes. Formulations for inhalation administration can contain as excipients, for example, lactose, or can be aqueous solutions containing, for example, polyoxyethylene-9-lauryl ether, glycocholate and deoxycholate, or oily solutions for administration in the form of nasal drops, or as a gel to be applied intranasally.

Formulations of the present invention suitable for oral administration can be in the form of: discrete units such as capsules, gelatin capsules, sachets, tablets, troches, or lozenges, each containing a predetermined amount of the drug; a powder or granular composition; a solution or a suspension in an aqueous liquid or non-aqueous liquid; or an oil-in-water emulsion or a water-in-oil emulsion. The drug can also be administered in the form of a bolus, electuary or paste. A tablet can be made by compressing or molding the drug optionally with one or more accessory ingredients. Compressed tablets can be prepared by compressing, in a suitable machine, the drug in a free-flowing form such as a powder or granules, optionally mixed by a binder, lubricant, inert diluent, surface active or dispersing agent. Molded tablets can be made by molding, in a suitable machine, a mixture of the powdered drug and suitable carrier moistened with an inert liquid diluent.

Oral compositions generally include an inert diluent or an edible carrier. For the purpose of oral therapeutic administration, the active compound can be incorporated with excipients. Oral compositions prepared using a fluid carrier for use as a mouthwash include the compound in the fluid carrier and are applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of the drug which can be in microcrystalline form, for example, in the form of an aqueous microcrystalline suspension. Liposomal formulations or biodegradable polymer systems can also be used to present the drug for both intra-articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops. Formulations for topical administration to the skin surface can be prepared by dispersing the drug with a dermatologically acceptable carrier such as a lotion, cream, ointment or soap. Particularly useful are carriers capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used.

For inhalation treatments, inhalation of powder (self-propelling or spray formulations) dispensed with a spray can, a nebulizer, or an atomizer can be used. Such formulations can be in the form of a fine powder for pulmonary administration from a powder inhalation device or self-propelling powder-dispensing formulations. In the case of self-propelling solution and spray formulations, the effect can be achieved either by choice of a valve having the desired spray characteristics (i.e., being capable of producing a spray having the desired particle size) or by incorporating the active ingredient as a suspended powder in controlled particle size. For administration by inhalation, the compounds also can be delivered in the form of an aerosol spray from pressured container or dispenser which contains a suitable propellant, e.g., a gas such as carbon dioxide, or a nebulizer.

Systemic administration also can be by transmucosal or transdermal means. For transmucosal or transdermal administration, penetrants appropriate to the barrier to be permeated are used in the formulation. Such penetrants generally are known in the art, and include, for example, for transmucosal administration, detergents and bile salts. Transmucosal administration can be accomplished through the use of nasal sprays or suppositories. For transdermal administration, the active compounds typically are formulated into ointments, salves, gels, or creams as generally known in the art.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

Where adhesion to a tissue surface is desired, the molecule can include the drug dispersed in a fibrinogen-thrombin composition or other bioadhesive. The molecule then can be painted, sprayed or otherwise applied to the desired tissue surface. Alternatively, the molecules can be formulated for parenteral or oral administration to humans or other mammals, for example, in therapeutically effective amounts, e.g., amounts which provide appropriate concentrations of the drug to target tissue for a time sufficient to induce the desired effect.

Active molecules identified or designed by the methods described herein can be administered to individuals to treat disorders (prophylactically or therapeutically). In conjunction with such treatment, pharmacogenomics (i.e., the study of the relationship between an individual's genotype and that individual's response to a foreign compound or drug) can be considered. Differences in metabolism of therapeutics can lead to severe toxicity or therapeutic failure by altering the relation between dose and blood concentration of the pharmacologically active drug. Thus, a physician or clinician can consider applying knowledge obtained in relevant pharmacogenomics studies in determining whether to administer a drug as well as tailoring the dosage and/or therapeutic regimen of treatment with the drug.

In therapeutic use for treating, or combating, bacterial infections in mammals, the molecules or pharmaceutical compositions thereof will be administered orally, parenterally and/or topically at a dosage to obtain and maintain a concentration, that is, an amount, or blood-level or tissue level of active component in the animal undergoing treatment which will be anti-microbially effective. To be microbially effective, the molecule is present in or on the recipient in an amount sufficient to elicit biological activity, for example, anti-microbial activity, anti-fungal activity, anti-viral activity, anti-parasitic activity, anti-proliferative activity, anti-inflammatory activity, or ameliorating a symptom of a gastrointestinal motility disorder. Generally, an effective amount of dosage of active molecule will be in the range of from about 0.1 to about 100, more preferably from about 1.0 to about 50 mg/kg of body weight/day. The amount administered will also likely depend on such variables as the type and extent of disease or indication to be treated, the overall health status of the particular patient, the relative biological efficacy of the compound delivered, the formulation of the drug, the presence and types of excipients in the formulation, and the route of administration. Also, it is to be understood that the initial dosage administered can be increased beyond the above upper level in order to rapidly achieve the desired blood-level or tissue level, or the initial dosage can be smaller than the optimum and the daily dosage can be progressively increased during the course of treatment depending on the particular situation. If desired, the daily dose can also be divided into multiple doses for administration, for example, two to four times per day.

In light of the foregoing general discussion, the specific examples presented below are illustrative only and are not intended to limit the scope of the invention. Other generic and specific configurations will be apparent to those persons skilled in the art.

III. Examples

Example 1

Three-Dimensional Structure of a RNA Microhelix when Associated with the Large Ribosomal Subunit Ribosomes were purified and crystallized as described previously (U.S. Patent Application Publication No. US 2002/0086308 A1). Crystals containing *H. marismortui* large ribosomal subunits complexed with the RNA microhelix of Formula I, were obtained by soaking pre-formed, large-subunit crystals in stabilizing buffers containing the RNA microhelix of Formula I.

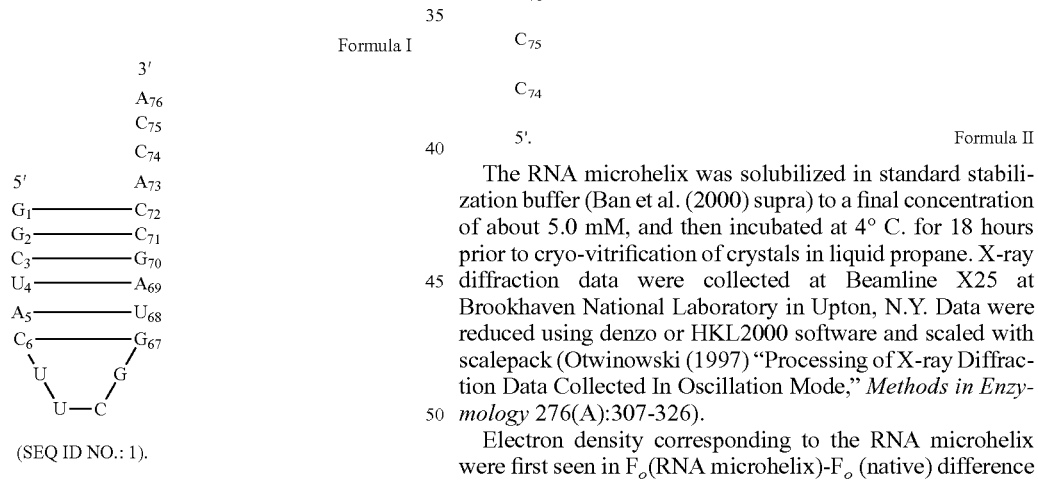

Formula I (SEQ ID NO.: 1).

The RNA microhelix was solubilized in standard stabilization buffer (Ban et al. (2000) *Science* 289: 905-920) to a final concentration of about 4.0 mM, and then incubated at 4° C. for 18 hours prior to cryo-vitrification of crystals in liquid propane. X-ray diffraction data were collected at Beamline 14-4 at the European Radiation Synchrotron Facility in Grenoble, France. Data were reduced using denzo or HKL2000 software and scaled with scalepack (Otwinowski (1997) "Processing of X-ray Diffraction Data Collected In Oscillation Mode," *Methods in Enzymology* 276(A):307-326).

Electron density corresponding to the RNA microhelix were first seen in $F_o$(RNA microhelix)-$F_o$(native) difference Fourier maps at 3.2 Å resolution calculated from data collected at beamline 14-4 at the European Radiation Synchrotron Facility in Grenoble, France. The RNA microhelix model initially was fit into $F_o$-$F_o$ difference electron density maps. The structures of the RNA microhelix complexed with these crystals was determined at 3.2 Å resolution from difference Fourier maps calculated initially using observed diffraction amplitudes from the native and complex crystals, [$F_o$(complex)-$F_o$(native)], and then the co-ordinates of the entire complex were refined. The structures of these complexes were refined using CNS (Brünger et al. (1998) *Acta Cryst.* D54: 905-921) for rigid body refinement, energy minimization, and B-factor refinement of the entire native ribosome structure including the antibiotic, and by manual modifications of only the immediate area surrounding the bound RNA microhelix. Nonisomorphous differences distant from the RNA microhelix were ignored. The refinement process then was repeated iteratively on the RNA microhelix-containing model.

Example 2

Three-Dimensional Structure of a RNA Microhelix when Associated with the Large Ribosomal Subunit Ribosomes were purified and crystallized as described previously (U.S. Patent Application Publication No. US 2002/0086308 A1). Crystals containing *H. marismortui* large ribosomal subunits complexed with the RNA microhelix of Formula II, were obtained by soaking pre-formed, large-subunit crystals in stabilizing buffers containing the RNA microhelix of Formula II.

3'

$A_{76}$ $C_{75}$ $C_{74}$

5'.   Formula II

The RNA microhelix was solubilized in standard stabilization buffer (Ban et al. (2000) supra) to a final concentration of about 5.0 mM, and then incubated at 4° C. for 18 hours prior to cryo-vitrification of crystals in liquid propane. X-ray diffraction data were collected at Beamline X25 at Brookhaven National Laboratory in Upton, N.Y. Data were reduced using denzo or HKL2000 software and scaled with scalepack (Otwinowski (1997) "Processing of X-ray Diffraction Data Collected In Oscillation Mode," *Methods in Enzymology* 276(A):307-326).

Electron density corresponding to the RNA microhelix were first seen in $F_o$(RNA microhelix)-$F_o$ (native) difference Fourier maps at 3.0 Å resolution calculated from data collected at Beamline X25 at Brookhaven National Laboratory in Upton, N.Y. The RNA microhelix model initially was fit into $F_o$-$F_o$ difference electron density maps. The structures of the RNA microhelix complexed with these crystals was determined at 3.0 Å resolution from difference Fourier maps calculated initially using observed diffraction amplitudes from the native and complex crystals, [$F_o$(complex)-$F_o$(native)], and then the co-ordinates of the entire complex were refined. The structures of these complexes were refined using CNS (Brünger et al. (1998) *Acta Cryst.* D54: 905-921) for rigid body refinement, energy minimization, and B-factor refinement of the entire native ribosome structure including the antibiotic, and by manual modifications of only the immediate area surrounding the bound RNA microhelix. Nonisomorphous differences distant from the RNA microhelix were ignored. The refinement process then was repeated iteratively on the RNA microhelix-containing model.

Example 3

Additional Three-Dimensional Structures of RNA Microhelices when Associated with the Large Ribosomal Subunit Using the general procedures of Example 1, crystals containing *H. marismortui* large ribosomal subunits complexed with other RNA microhelices (for example, a 5' ACCA 3' RNA microhelix) are obtained. The three-dimensional structures of these crystal complexes can be obtained as described in Examples 1 and 2. The resulting structures can also be used to design other candidate molecules useful as protein synthesis modulators.

INCORPORATION BY REFERENCE

The entire disclosure of each of the patent documents, scientific articles, and atomic co-ordinates (including, without limitation, the atomic co-ordinate sets contained on Disk No. 1) referred to herein is incorporated by reference herein for all purposes as though the content of each of the patent documents, scientific articles, and atomic co-ordinates were included herein.

Disk No. 1 was created on Jul. 22, 2003, and is identified as containing the following three files:

| Disk No. 1: | | |
|---|---|---|
| File: | | Size (in bytes) |
| FOLDERA: | | |
| <DIR> | | |
| <DIR> | | |
| 1JJ2.pdb | | 8,270,586 |
| | FOLDERB: | |
| <DIR> | | |
| <DIR> | | |
| microhelix.pdb | | 7,609,736 |
| | FOLDERC: | |
| <DIR> | | |
| <DIR> | | |
| microhelixa.pdb | | 7,688,935 |

EQUIVALENTS

The invention can be embodied in other specific forms without departing form the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method of identifying a molecule that binds to a large ribosomal subunit, the method comprising the steps of:
   (a) providing a molecular model of at least a portion of an RNA microhelix binding site of a large subunit of a ribosome created from (i) the atomic co-ordinates for the *Haloarcula marismortui* large ribosomal subunit found on Replacement Disk 1 under file name microhelix.txt or microhelixa.txt, or (ii) atomic co-ordinates derived by molecular modeling from the *Haloarcula marismortui* atomic co-ordinates found on Replacement Disk 1 under file name microhelix.txt or microhelixa.txt;
   (b) using the molecular model to identify a candidate molecule that binds to at least a portion of the RNA microhelix binding site of the molecular model, wherein the RNA microhelix binding site comprises at least a portion of the E-site of the large ribosomal subunit; and
   (c) producing the candidate molecule identified in step (b).

2. The method of claim 1, wherein in step (a)(ii), the molecular model is generated by molecular modeling.

3. The method of claim 2, wherein the molecular model is generated by homology modeling.

4. The method of claim 2, wherein the molecular model is generated by molecular replacement.

5. The method of claim 1, wherein the molecular model comprises residues that are conserved among one or more prokaryotic organisms.

6. The method of claim 5, wherein the candidate molecule binds specifically to the RNA microhelix binding site of the molecular model.

7. The method of claim 5, wherein the candidate molecule stereochemically interfits with the RNA microhelix binding site of the molecular model.

8. The method of claim 1 comprising the additional step of determining whether the candidate molecule modulates ribosomal activity.

9. The method of claim 1 comprising the additional step of identifying a modified candidate molecule that binds the RNA microhelix binding site.

10. The method of claim 9 comprising the additional step of producing the modified candidate molecule.

11. The method of claim 10 comprising the additional step of determining whether the modified candidate molecule modulates ribosomal activity.

12. The method of claim 11 comprising the additional step of producing the modified candidate molecule.

13. The method of claim 1, wherein the candidate molecule is an antibiotic.

14. The method of claim 11, wherein the modified candidate molecule is an antibiotic.

15. The method of claim 1, wherein the molecular model is in an electronic form.

* * * * *

SEQUENCE LISTING

```
<160> NUMBER OF SEQ ID NOS: 8

<210> SEQ ID NO 1
<211> LENGTH: 20
<212> TYPE: RNA
<213> ORGANISM: Artificial sequence
<220> FEATURE:
<223> OTHER INFORMATION: RNA microhelix of Formula I

<400> SEQUENCE: 1
ggcuacuucg guagccacca                                               20

<210> SEQ ID NO 2
<211> LENGTH: 11
<212> TYPE: RNA
<213> ORGANISM: Artificial sequence
<220> FEATURE:
<223> OTHER INFORMATION: One strand of a possible RNA microhelix
<220> FEATURE:
<221> NAME/KEY: misc_feature
<222> LOCATION: (1)..(8)
<223> OTHER INFORMATION: n = A, G, U, C

<400> SEQUENCE: 2
nnnnnnnncc a                                                        11

<210> SEQ ID NO 3
<211> LENGTH: 25
<212> TYPE: RNA
<213> ORGANISM: Artificial sequence
<220> FEATURE:
<223> OTHER INFORMATION: Possible RNA microhelix structure
```

```
<220> FEATURE:
<221> NAME/KEY: misc_feature
<222> LOCATION: (1)..(22)
<223> OTHER INFORMATION: n = A, G, U, C
<220> FEATURE:
<221> NAME/KEY: misc_feature
<222> LOCATION: (8)..(14)
<223> OTHER INFORMATION: up to five nucleotides may be absent

<400> SEQUENCE: 3 nnnnnnnnn nnnnnnnnn nncca                                              25

<210> SEQ ID NO 4
<211> LENGTH: 23
<212> TYPE: RNA
<213> ORGANISM: Artificial sequence
<220> FEATURE:
<223> OTHER INFORMATION: Possible RNA microhelix structure
<220> FEATURE:
<221> NAME/KEY: misc_feature
<222> LOCATION: (1)..(20)
<223> OTHER INFORMATION: n = A, G, U, C
<220> FEATURE:
<221> NAME/KEY: misc_feature
<222> LOCATION: (7)..(13)
<223> OTHER INFORMATION: up to five nucleotides may be absent

<400> SEQUENCE: 4 nnnnnnnnn nnnnnnnnn nn cca                                             23

<210> SEQ ID NO 5
<211> LENGTH: 21
<212> TYPE: RNA
<213> ORGANISM: Artificial sequence
<220> FEATURE:
<223> OTHER INFORMATION: Possible RNA microhelix structure
<220> FEATURE:
<221> NAME/KEY: misc_feature
<222> LOCATION: (1)..(18)
<223> OTHER INFORMATION: n = A, G, U, C
<220> FEATURE:
<221> NAME/KEY: misc_feature
<222> LOCATION: (6)..(12)
<223> OTHER INFORMATION: up to five nucleotides may be absent

<400> SEQUENCE: 5 nnnnnnnnn nnnnnnncc a                                                  21

<210> SEQ ID NO 6
<211> LENGTH: 19
<212> TYPE: RNA
<213> ORGANISM: Artificial sequence
<220> FEATURE:
<223> OTHER INFORMATION: Possible RNA microhelix structure
<220> FEATURE:
<221> NAME/KEY: misc_feature
<222> LOCATION: (1)..(16)
<223> OTHER INFORMATION: n = A, G, U, C
<220> FEATURE:
<221> NAME/KEY: misc_feature
<222> LOCATION: (5)..(11)
<223> OTHER INFORMATION: up to five nucleotides may be absent

<400> SEQUENCE: 6 nnnnnnnnn nnnnnncca                                                    19

<210> SEQ ID NO 7
<211> LENGTH: 25
<212> TYPE: RNA
<213> ORGANISM: Artificial sequence
<220> FEATURE:
<223> OTHER INFORMATION: Possible RNA microhelix structure
```

```
<220> FEATURE:
<221> NAME/KEY: misc_feature
<222> LOCATION: (1)..(22)
<223> OTHER INFORMATION: n = A, G, U, C
<220> FEATURE:
<221> NAME/KEY: misc_feature
<222> LOCATION: (1)..(7)
<223> OTHER INFORMATION: up to seven nucleotides may be absent, but must
      be the same number as the number of absent nuclotides from 15 to
      21
<220> FEATURE:
<221> NAME/KEY: misc_feature
<222> LOCATION: (8)..(14)
<223> OTHER INFORMATION: 0, 2, 3, 4, 5, 6 or 7 nucleotides may be
      absent.  If the number of absent nucleotides between positions 1
      to 7 and 15 to 21 is seven, seven nucleotides must be absent.
<220> FEATURE:
<221> NAME/KEY: misc_feature
<222> LOCATION: (15)..(21)
<223> OTHER INFORMATION: up to seven nucleotides may be absent, but must
      be the same number as the number of absent nucleotides from
      positions 1 to 7
<220> FEATURE:
<221> NAME/KEY: misc_feature
<222> LOCATION: (22)..(22)
<223> OTHER INFORMATION: nucleotide may be absent
<220> FEATURE:
<221> NAME/KEY: misc_feature
<222> LOCATION: (23)..(23)
<223> OTHER INFORMATION: nucleotide may be absent

<400> SEQUENCE: 7
nnnnnnnnnn nnnnnnnnnn nncca                                           25

<210> SEQ ID NO 8
<211> LENGTH: 79
<212> TYPE: RNA
<213> ORGANISM: Artificial sequence
<220> FEATURE:
<223> OTHER INFORMATION: Potential RNA microhelix sequence
<220> FEATURE:
<221> NAME/KEY: misc_feature
<222> LOCATION: (1)..(7)
<223> OTHER INFORMATION: n = A, G, U, C
<220> FEATURE:
<221> NAME/KEY: misc_feature
<222> LOCATION: (9)..(10)
<223> OTHER INFORMATION: n = A, G, U, C
<220> FEATURE:
<221> NAME/KEY: misc_feature
<222> LOCATION: (12)..(13)
<223> OTHER INFORMATION: n = A, G, U, C
<220> FEATURE:
<221> NAME/KEY: misc_feature
<222> LOCATION: (16)..(18)
<223> OTHER INFORMATION: n = A, G, U, C
<220> FEATURE:
<221> NAME/KEY: misc_feature
<222> LOCATION: (21)..(23)
<223> OTHER INFORMATION: n = A, G, U, C
<220> FEATURE:
<221> NAME/KEY: misc_feature
<222> LOCATION: (25)..(26)
<223> OTHER INFORMATION: n = A, G, U, C
<220> FEATURE:
<221> NAME/KEY: misc_feature
<222> LOCATION: (28)..(34)
<223> OTHER INFORMATION: n = A, G, U, C
<220> FEATURE:
<221> NAME/KEY: misc_feature
<222> LOCATION: (37)..(39)
<223> OTHER INFORMATION: n = A, G, U, C
<220> FEATURE:
<221> NAME/KEY: misc_feature
<222> LOCATION: (41)..(50)
<223> OTHER INFORMATION: n = A, G, U, C
```

```
<220> FEATURE:
<221> NAME/KEY: misc_feature
<222> LOCATION: (52)..(55)
<223> OTHER INFORMATION: n = A, G, U, C
<220> FEATURE:
<221> NAME/KEY: misc_feature
<222> LOCATION: (57)..(57)
<223> OTHER INFORMATION: n = ribothymidine
<220> FEATURE:
<221> NAME/KEY: misc_feature
<222> LOCATION: (62)..(62)
<223> OTHER INFORMATION: n = A, G, U, C
<220> FEATURE:
<221> NAME/KEY: misc_feature
<222> LOCATION: (65)..(76)
<223> OTHER INFORMATION: n = A, G, U, C

<400> SEQUENCE: 8
nnnnnnnunn ynnarnnngg nnnannrnnn nnnnyunnnr nnnnnnnnnn cnnnngnucr      60
anycnnnnnn nnnnnncca                                                  79
```